(12) United States Patent
Van Ness et al.

(10) Patent No.: US 6,884,586 B2
(45) Date of Patent: Apr. 26, 2005

(54) METHYLATION ANALYSIS USING NICKING AGENTS

(75) Inventors: Jeffrey Van Ness, Claremont, CA (US); David J. Galas, Claremont, CA (US); Lori K. Van Ness, Claremont, CA (US)

(73) Assignee: Keck Graduate Institute, Claremont, CA (US)

( * ) Notice: Subject to any disclaimer, the term of this patent is extended or adjusted under 35 U.S.C. 154(b) by 254 days.

(21) Appl. No.: 10/197,616

(22) Filed: Jul. 15, 2002

(65) Prior Publication Data

US 2003/0152952 A1 Aug. 14, 2003

Related U.S. Application Data

(60) Provisional application No. 60/305,637, filed on Jul. 15, 2001, and provisional application No. 60/345,445, filed on Jan. 2, 2002.

(51) Int. Cl.[7] .................................................. C12Q 1/68
(52) U.S. Cl. ............................................................ 435/6
(58) Field of Search ................................ 435/5, 6, 91.2, 435/320.1, 69.1; 536/23.1, 23.4

(56) References Cited

U.S. PATENT DOCUMENTS

| | | | | |
|---|---|---|---|---|
| 4,935,357 A | 6/1990 | Szybalski | ..................... | 435/91 |
| 5,011,769 A | 4/1991 | Duck et al. | ..................... | 435/6 |
| 5,455,166 A | * 10/1995 | Walker | ..................... | 435/91.2 |
| 5,470,723 A | 11/1995 | Walker et al. | ............. | 435/91.2 |
| 5,523,204 A | 6/1996 | Singer et al. | .................. | 435/5 |
| 5,547,861 A | 8/1996 | Nadeau et al. | ............. | 435/91.2 |
| 5,561,044 A | 10/1996 | Walker et al. | ................. | 435/6 |
| 5,624,825 A | 4/1997 | Walker et al. | ............. | 435/91.2 |
| 5,631,147 A | 5/1997 | Lohman et al. | ............ | 435/91.2 |
| 5,648,211 A | 7/1997 | Fraiser et al. | .................. | 435/6 |
| 5,702,926 A | 12/1997 | Fraiser et al. | ............. | 435/91.2 |
| 5,712,214 A | 1/1998 | Huang et al. | ................. | 502/37 |
| 5,733,752 A | 3/1998 | Lohman et al. | ............ | 435/91.2 |
| 5,736,365 A | 4/1998 | Walker et al. | ............. | 435/91.2 |
| 5,744,311 A | 4/1998 | Fraiser et al. | .................. | 435/6 |
| 5,756,702 A | 5/1998 | Lohman et al. | .......... | 536/24.33 |
| 5,811,269 A | 9/1998 | Nadeau et al. | ............. | 435/91.1 |
| 5,837,469 A | 11/1998 | Harris | ........................... | 435/6 |
| 5,849,547 A | 12/1998 | Cleuziat et al. | .......... | 435/91.21 |
| 5,866,336 A | 2/1999 | Nazarenko et al. | ............ | 435/6 |
| 5,916,779 A | 6/1999 | Pearson et al. | ............ | 435/91.2 |
| 5,919,630 A | 7/1999 | Nadeau et al. | ................. | 435/6 |
| 5,928,869 A | 7/1999 | Nadeau et al. | ................. | 435/6 |
| 5,958,700 A | 9/1999 | Nadeau et al. | ................. | 435/6 |
| 5,962,273 A | 10/1999 | Durmowicz et al. | ....... | 435/91.1 |
| 5,968,786 A | 10/1999 | Dunn et al. | ............... | 435/91.53 |
| 5,976,805 A | 11/1999 | You | .............................. | 435/6 |
| 5,985,569 A | 11/1999 | Foxall et al. | .................. | 435/6 |
| 6,004,754 A | 12/1999 | You | .............................. | 435/6 |
| 6,054,279 A | 4/2000 | Nadeau et al. | ................. | 435/6 |
| 6,063,604 A | 5/2000 | Wick et al. | ................ | 435/91.2 |
| 6,087,133 A | 7/2000 | Dattagupta et al. | ........ | 435/91.1 |
| 6,191,267 B1 | * 2/2001 | Kong et al. | ................. | 536/23.4 |
| 6,200,756 B1 | 3/2001 | Herman et al. | ................ | 435/6 |
| 6,214,587 B1 | 4/2001 | Dattagupta et al. | ........ | 435/91.2 |
| 6,218,119 B1 | * 4/2001 | Kuiper et al. | ................... | 435/6 |
| 6,218,125 B1 | 4/2001 | Foxall et al. | ................... | 435/6 |
| 6,221,592 B1 | 4/2001 | Schwartz et al. | ............... | 435/6 |
| 6,238,868 B1 | 5/2001 | Carrino et al. | ................. | 435/6 |
| 6,238,884 B1 | 5/2001 | Short et al. | ................ | 435/69.1 |
| 6,258,546 B1 | 7/2001 | McMillian et al. | ............ | 435/6 |
| 6,316,200 B1 | 11/2001 | Nadeau et al. | ................. | 435/6 |
| 2001/0039039 A1 | 11/2001 | Weissman et al. | ......... | 435/91.1 |
| 2002/0006643 A1 | 1/2002 | Kayyem et al. | ........... | 435/91.2 |

FOREIGN PATENT DOCUMENTS

| | | |
|---|---|---|
| EP | 0500224 | 8/1992 |
| EP | 0585660 | 3/1994 |
| EP | 0640691 | 3/1995 |
| EP | 0819768 | 1/1998 |
| EP | 0878553 | 11/1998 |
| WO | WO 89/10415 | 11/1989 |
| WO | WO 95/25180 | 9/1995 |
| WO | WO97/11196 | 3/1997 |
| WO | WO97/35026 | 9/1997 |
| WO | WO98/00566 | 1/1998 |
| WO | WO99/49081 | 9/1999 |
| WO | WO 00/15849 | 3/2000 |
| WO | WO 00/18238 | 4/2000 |
| WO | WO00/28084 | 5/2000 |
| WO | WO 00/31294 | 6/2000 |
| WO | WO 00/31300 | 6/2000 |
| WO | WO00/60919 | 10/2000 |
| WO | WO00/61720 | 10/2000 |
| WO | WO00/61803 | 10/2000 |
| WO | WO00/62036 | 10/2000 |
| WO | WO00/63437 | 10/2000 |
| WO | WO 01/90419 | 11/2001 |
| WO | WO 01/98527 | 12/2001 |

OTHER PUBLICATIONS

Marianne Frommer, Louise E. McDonald et al. A genomic sequencing protocol that yields a positive display of 5–methylcytosine residues in individual DNA strands. 1992. Proc. Natl. Acad. Sci. USA 89: pp. 1827–1831.*

Abramson et al., "Nucleic Acid Amplification Technologies," *Curr. Opin. Biotech.* 4:41–47, 1993.

Akduman et al., "Evaluation of a Strand Displacement Amplification Assay (BD Probe Tech–SDA) for Detection of *Neisseria gonorrhoeae* in Urine Specimens," *J. Clin. Microbiol.* 40(1):281–283, Jan. 2002.

Andras et al., "Strategies for Signal Amplification in Nucleic Acid Detection," *Mol. Biotech.* 19:29–44, 2001.

Badak et al., "Confirmation of the Presence of *Mycobacterium tuberculosis* and Other Mycobacteria in Mycobacterial Growth Indicator Tubes (MGIT) by Multiplex Strand Displacement Amplification," *J. Clin. Microbiol.* 35(5):1239–43, May 1997.

(Continued)

Primary Examiner—Kenneth R. Horlick
Assistant Examiner—Heather G. Calamita
(74) *Attorney, Agent, or Firm*—Seed IP Law Group PLLC

(57) ABSTRACT

The present invention provides methods and compositions for nucleic acid methylation analysis using nicking agents.

49 Claims, 9 Drawing Sheets

OTHER PUBLICATIONS

Bergmann et al., "Clinical Evaluation of the BDProbeTec Strand Displacement Amplification Assay for Rapid Diagnosis of Tuberculosis," *J. of Clin. Microbiol.* 36(9):2766–2768, Sep. 1998.

Besnier et al., "Converting MlyI Endonuclease Into a Nicking Enzyme by Changing Its Oligomerization State," *EMBO Reports* 2(9): 782–786, 2001.

Chan et al., "Performance Characteristics of the Becton Dickinson ProbeTec System for Direct Detection of *Chlamydia trachomatis* and *Neisseria gonorrhoeae* in Male and Female Urine Specimens in Comparison With the Roche Cobas System," *Arch. Pathol. Lab. Med.* 124:1649–1652, Nov. 2000.

Down et al., "Detection of *Mycobacterium tuberculosis* in Respiratory Specimens by Strand Displacement Amplification of DNA," *J. Clin. Microbiol.* 34(4):860–865, Apr. 1996.

Edman et al., "Pathogen Analysis and Genetic Predisposition Testing Using Microelectronic Arrays and Isothermal Amplification," *J. Invest. Med.* 48(2):93–101, Mar. 2000.

Gelb et al., "Editorial Summary of the Pre–symposium Workshop on the Contemporary Assessment of Technologies," *Biologicals* 24:177–186, 1996.

Hellyer et al., "Detection of Viable *Mycobacterium tuberculosis* by Reverse Transcriptase–Strand Displacement Amplification of mRNA," *J. Clin. Microbiol.* 37(3):518–523, Mar. 1999.

Hellyer et al., "Specificity of IS6110–Based Amplification Assays for *Mycobacterium tuberculosis* Complex," *J. Clin. Microbiol.* 34(11):2843–2846, Nov. 1996.

Hellyer et al., "Strand Displacement Amplification and the Polymerase Chain Reaction for Monitoring Response to Treatment in Patients with Pulmonary Tuberculosis," *J. Infec. Diseases* 173:934–941, Apr. 1996.

Higgins et al., "The Nicking Endonuclease N.BstNBI is closely related to Type IIs Restriction Endonucleases MLyI and PleI," *Nucl. Acids Res.* 29(12):2492–2501, 2001.

Huang et al., "Multiple Cleavage Activities of Endonuclease V from *Thermotoga maritima* Recognition an Strand Nicking Mechanism," *Biochemistry* 40:8738–8748, 2001.

Ichiyama et al., "Diagnostic Value of the Strand Displacement Amplification Method Compared to Those of Roche Amplicor PCR and Culture for Detecting Mycobacteria in Sputum Samples," *J. of Clin. Microbiol.* 35(12):3082–3085, Dec. 1997.

Kim et al., "Site–Specific Cleavage of DNA–RNA Hybrids by Zinc Finger/FokI Cleavage Domain Fusions," *Gene* 203:43–49, 1997.

Laken et al., "Genotyping by Mass Spectometric Analysis of Short DNA Fragments," *Nature Biotechnology* 16:1352–1356, Dec. 1998.

Lavin et al, "A Mammalian Nicking Endonuclease," *Biochem.* 15(11):2409–2414, 1976.

Lisby, Gorm, "Application of Nucleic Acid Amplification in Clinical Microbiology," *Mol. Biotechnol.* 12:75–99, 1999.

Little et al., "Strand Displacement Amplification and Homogeneous Real–Time Detection Incorporated in a Second–Generation DNA Probe System, BDProbeTecET," *Clin. Chem.* 45(6):777–784, 1999.

Little et al., "Nucleotide Sequence and Strand Displacement Amplification of the 70K Protein Gene From Mycobacteria," *Mol. and Cell. Probes* 8:375–384, 1994.

Lizardi et al., "Mutation Detection and Single–Molecule Counting Using Isothermal Rolling–Circle Amplification," *Nature Genetics* 19:225–232, Jul. 1998.

Mehrpouyan et al., A Rapid and Sensitive Method for Non–Isotopic Quantitation of HIV–1 RNA Using Thermophilic SDA and Flow Cytometry, *Mol. and Cell. Probes* 11:337–347, 1997.

Milla et al., "Use of the Restriction Enzyme AvaI and Exo⁻Bst Polymerase in Strand Displacement Amplification," *BioTechniques* 24(3):392–396, Mar. 1998.

Morgan et al., "Characterization of the Specific DNA Nicking Activity of Restriction Endonuclease N.BstNBI," *Biol. Chem.* 381:1123–1125, Nov. 2000.

Nadeau et al., "Real–Time, Sequence–Specific Detection of Nucleic Acids During Strand Displacement Amplification," *Anal. Biochem.* 276:177–87, 1999.

Notomi et al., "Loop–Mediated Isothermal Amplification of DNA," *Nuc. Acids Res.* 28(12):I–vii, 2000.

Nuovo, Gerard, "In Situ Strand Displacement Amplification: An Improved Technique for the Detection of Low Copy Nucleic Acids," *Diag. Mol. Path.* 9(4):195–202, 2000.

Nycz et al., "Quantitative Reverse Transcription Strand Displacement Amplification: Quantitation of Nucleic Acids Using an Isothermal Amplification Technique," *Anal. Biochem.* 259:226–234, 1998.

Pfyffer et al., "Performance Characteristics of the BDProbeTec System for Direct Detection of *Mycobacterium tuberculosis* Complex in Respiratory Specimens," *J. Clin. Microbiol.* 37(1):137–140, Jan. 1999.

Seckinger, Daniel, "Strand Displacement Amplification and Fluorescence Polarization," *Clin. Chem.* 42(10):1720, 1996.

Spargo et al., "Chemiluminescent Detection of Strand Displacement Amplified DNA from Species Comprising the *Mycobacterium tuberculosis* Complex," *Mol. and Cell. Probes* 7:395–404, 1993.

Spargo et al., "Detection of *M. tuberculosis* DNA Using Thermophilic Strand Displacement Amplification," *Mol. and Cell. Probes* 10:247–256, 1996.

Spears et al., "Simultaneous Strand Displacement Amplification and Fluorescence Polarization Detection of *Chlamydia trachomatis* DNA," *Anal. Biochem.* 247:130–37, 1997.

Stahl et al., "Introduction of Asymmetry in the Naturally Symmetric Restriction Endonuclease EcoRV to Investigate Intersubunit Communication in the Homodimeric Protein," *PNAS USA* 93:6175–6180, Jun. 1996.

Thomas et al., "Amplification of Padlock Probes for DNA Diagnostics by Cascade Rolling Circle Amplification or the Polymerase Chain Reaction," *Arch. Pathol. Lab. Med.* 123:1170–1176, Dec. 1999.

Van Dyck et al., "Detection of *Chlamydia trachomatis* and *Neisseria gonorrhoeae* by Enzyme Immunoassay, Culture, and Three Nucleic Acid Amplification Tests," *J. Clin. Microbiol.* 39(5):1751–1756, May 2001.

Walker et al., "DNA Detection by Strand Displacement Amplification and Fluorescence Polarization With Signal Enhancement Using a DNA Binding Protein," *Nucl. Acids Res.* 24(2):348–353, 1996.

Walker et al., "A DNA Probe Assay Using Strand Displacement Amplification (SDA) and Filtration to Separate Reacted and Unreacted Detector Probes," *Mol. and Cell. Probes* 9:399–403, 1995.

Walker et al., "Detection of *Mycobacterium tuberculosis* DNA With Thermophilic Strand Displacement Amplification and Fluorescence Polarization," *Clin. Chem.* 42(10):1604–1608, 1996.

Walker, "Empirical Aspects of Strand Displacement Amplification," *PCR Methods and Applic.* 3:1–6, 1993.

Walker et al., "Isothermal in Vitro Amplification of DNA by a Restriction Enzyme/DNA Polymerase System," *PNAS USA* 89:392–396, Jan. 1992.

Walker et al., "Multiplex Strand Displacement Amplification (SDA) and Detection of DNA Sequences from *Mycobacterium tuberculosis* and Other Mycobacteria," *Nucl. Acids Res.* 22(13):2670–2677, 1994.

Walker et al., "Strand Displacement Amplification–An Isothermal, in Vitro DNA Amplification Technique," *Nucl. Acids Res.* 20(7):1691–1696, 1992.

Walker et al., "Strand Displacement Amplification (SDA) and Transient–State Fluorescence Polarization Detection of *Mycobacterium tuberculosis* DNA," *Clin. Chem.* 42(1):9–13, 1996.

Walter et al., "Strand Displacement Amplification as an in Vitro Model for Rolling–Circle Replication: Deletion Formation and Evolution During Serial Transfer," *PNAS USA* 91:7937–7941, Aug. 1994.

Walter, Nils, "Modelling Evolution in Vitro Using Exo⁻Klenow Polymerase: Continuous Selection of Strand Displacement Amplified DNA that Binds an Oligodeoxynucleotide to Form a Triple–helix," *J. Mol. Biol.* 254:856–868, 1995.

Westin et al., "Antimicrobial Resistance and Bacterial Identification Utilizing a Microelectronic Chip Array," *J. Clin. Microbiol.* 39(3):1097–1104, Mar. 2001.

Westin et al., "Anchored Multiplex Amplification on a Microelectronic Chip Array," *Nat. Biotech.* 18:199–204, Feb. 2000.

Xu et al., "Engineering a Nicking Endonuclease NAlwI by Domain Swapping," *PNAS USA* 98(23):12990–12995, Nov. 6, 2001.

Zhang et al., "Detection of Rare DNA Targets by Isothermal Ramification Amplification," *Gene* 274:209–216, 2001.

Zhang et al., "Detection of *Chlamydia trachomatis* by Isothermal Ramification Amplification Method: a Feasibility Study," *J. Clin. Microbiol.* 40(1):128–132, Jan. 2002.

Zwadyk et al., "Rendering of Mycobacteria Safe for Molecular Diagnostic Studies and Development of a Lysis Method for Strand Displacement Amplification and PCR," *J. Clin. Microbiol.* 32(9):2140–2146, Sep. 1994.

\* cited by examiner

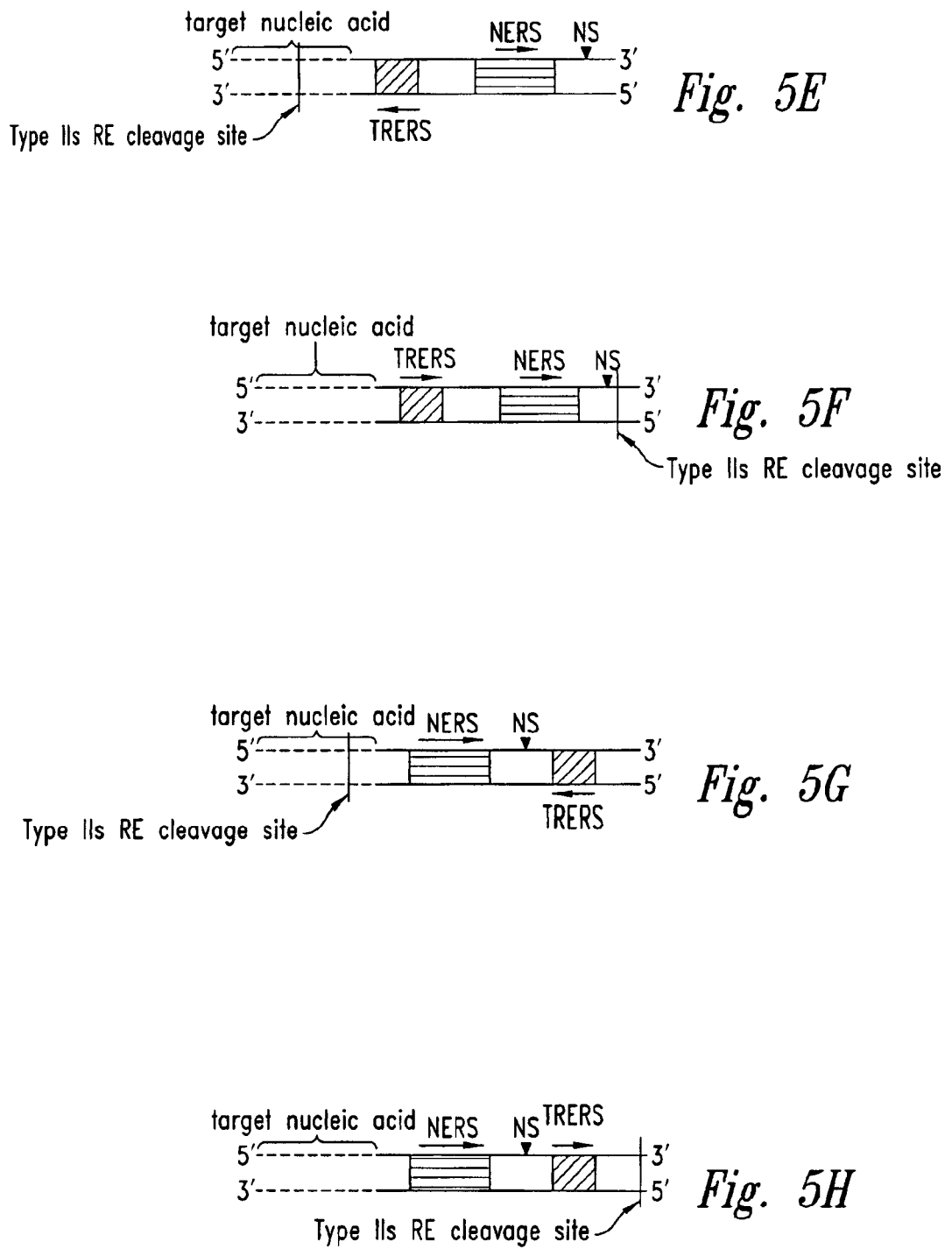

US 6,884,586 B2

METHYLATION ANALYSIS USING NICKING AGENTS

BACKGROUND OF THE INVENTION

1. Field of the Invention

This invention is related to the field of molecular biology, more particularly to methods and compositions involving nucleic acids, and still more particularly to methods and compositions related to methylation analysis using a nicking agent.

2. Description of the Related Art

DNA methylation is important to both prokaryotic and eukaryotic organisms. In prokaryotic organisms, it is involved in DNA replication. Lewin, *Genes VII*, Oxford University Press, pages 406–8, 2000. In eukaryotic organisms, DNA methylation participates in regulating gene expression, X-chromosome inactivation, genomic imprinting, cell differentiation and tumorigenesis. Rein et al., *Nucleic Acids Res.* 26: 2255–64, 1998. 5-Methylcytosine is the most abundant methylated nucleotide in eukaryotic cells; while in prokaryotic cells, the most prevalent methylated nucleotides are 5-methylcytosine and $N^6$-methyladenine. Id.

A number of methods have been developed for identifying methylated nucleotides in DNA genomes. These include the use of methylation-sensitive restriction endonucleases and differential base modification by bisulfite, hydrazine or permanganate. Among them, the bisulfite method offers both easy application and high sensitivity. Such high sensitivity is partially a result of PCR amplification of the target nucleic acids after bisulfite treatment. However, because nucleic acid amplification by PCR requires cycles of different temperatures to achieve cycles of denaturation and reannealing, the current bisulfite method requires means for providing cycles of different temperatures. Accordingly, there is a need in the art for a simpler method for determining DNA methylation states.

The present invention fulfills this and related needs. In contrast to previously known techniques, the present invention does not require multiple cycles of different temperatures for amplifying target nucleic acid fragments after being modified.

BRIEF SUMMARY OF THE INVENTION

In one aspect, the present invention provides a method for characterizing the methylation state of a target nucleic acid, comprising:

a. treating the target nucleic acid with a modifying agent that differentially modifies a nucleotide based on the methylation state of the nucleotide to provide a treated target nucleic acid;

b. providing a template double-stranded nucleic acid that comprises a nicking agent recognition sequence (NARS) and a portion of the treated target nucleic acid or an amplification product thereof if the target nucleic acid is single-stranded or a portion of one strand of the treated target nucleic acid if the target nucleic acid is double-stranded;

c. amplifying a single-stranded nucleic acid fragment in the presence of a nicking agent (NA) that recognizes the NARS, a DNA polymerase, and one or more deoxynucleoside triphosphate(s), wherein the amplifying uses a portion of the template double-stranded nucleic acid as a template; and d. characterizing the single-stranded nucleic acid fragment and thereby characterizing the methylation state of the single-stranded target nucleic acid.

In certain embodiments, the template nucleic acid is provided by the following steps:

(1) forming a mixture comprising the treated target nucleic acid, a first oligonucleotide primer (ODNP) and a second ODNP, wherein (a) if the target nucleic acid is single-stranded,
the first ODNP comprises a sequence of a sense strand of a NARS, and a nucleotide sequence at least substantially complementary to a first nucleotide sequence of the target nucleic acid,
the second ODNP comprises a sequence at least substantially identical to a second nucleotide sequence of the target nucleic acid, the second nucleotide sequence located 5' to the first nucleotide sequence; or (b) if the target nucleic acid is double-stranded having a first strand and a second strand,
the first ODNP comprises a sequence of a sense strand of a NARS and a nucleotide sequence at least substantially complementary to a first nucleotide sequence of the first strand of the target nucleic acid,
the second ODNP comprises a sequence at least substantially complementary to a second nucleotide sequence of the second strand of the target nucleic acid, the nucleotide sequence in the first strand of the target nucleic acid that corresponds to the second nucleotide sequence in the second strand of the target nucleic acid being located at 5' to the first nucleotide sequence in the first strand of the target nucleic acid; and (2) maintaining said mixture at conditions that amplify a template double-stranded nucleic acid that comprises the NARS.

In certain other embodiments, the template nucleic acid is provided by the following steps:

(a) if the target nucleic acid is single-stranded,
(i) synthesizing a completely complementary strand of the treated target nucleic acid to provide a double-stranded nucleic acid fragment, and
(ii) ligating an adaptor to the double-stranded nucleic acid fragment of step (i), wherein the adaptor comprises a NARS; or (b) if the target nucleic acid is double-stranded,
(i) ligating an adaptor to the treated target nucleic acid, wherein the adaptor comprises a NARS.

In some embodiments, the template nucleic acid is provided by the following steps:

(1) forming a mixture comprising
(A) the treated target nucleic acid, and
(B) an oligonucleotide primer that
i) comprises a sequence of the sense strand of a NARS, and
ii) is at least substantially complementary to a first portion of the treated target nucleic acid or to a first portion of one strand of the target nucleic acid; and (2) extending the oligonucleotide primer using
(A) a second portion of the treated single-stranded target nucleic acid located 5' to the first portion of the single-stranded target nucleic acid, or
(B) a second portion of the one strand of the treated double-stranded nucleic acid located 5' to the first portion of the one strand of the treated double-stranded nucleic acid
as a template to provide the template nucleic acid.

In certain embodiment, the template nucleic acid is provided by the following steps:
(1) forming a mixture comprising
  (A) the treated target nucleic acid,
  (B) an oligonucleotide primer that
    i) comprises a sequence of the sense strand of a NARS, and
    ii) is at least substantially complementary to a first portion of the treated target nucleic acid or to a first portion of one strand of the target nucleic acid; and
  (C) a partially double-stranded nucleic acid that
    i) comprises a double-stranded type IIs restriction endonuclease recognition sequence,
    ii) a 3' overhang that
      a) is at least substantially complementary to a second region of the single-stranded target nucleic acid located 5' to the first region of the single-stranded target nucleic acid, or
      b) is at least substantially complementary to a second region of the one strand of the double-stranded target nucleic acid located 5' to the second region of the one strand of the double-stranded target nucleic acid,
  under conditions that allow for hybridization between the oligonucleotide primer and the first region of the single-stranded target nucleic acid or of the one strand of the double-stranded nucleic acid and between the 3' overhang of the partially double-stranded nucleic acid and the second region of the single-stranded target nucleic acid or of the one strand of the double-stranded nucleic acid;
(2) digesting the single-stranded target nucleic acid or the one strand of the double-stranded target nucleic acid that have hybridized to the oligonucleotide primer and to the partially double-stranded nucleic acid in the second region; and
(3) extending from the 3' terminus of the oligonucleotide primer using the region between the first and second regions of the treated single-stranded target nucleic acid or between the first and second regions of the one strand of the treated double-stranded target nucleic acid as a template to provide the template nucleic acid.

In another aspect, the present invention provides a method for the multiplex characterization of methylation states of at least portions of target nucleic acids, comprising
  a. treating the target nucleic acids with a modifying agent that differentially modifies a nucleotide based on the methylation state of the nucleotide, to provide treated target nucleic acids;
  b. for each target nucleic acid, providing a template double-stranded nucleic acid that comprises a nicking agent recognition sequence (NARS) and a portion of the treated target nucleic acid or an amplification product thereof;
  c. amplifying single-stranded nucleic acid fragments in the presence of a nicking agent (NA) that recognizes the NARS, a DNA polymerase, and one or more deoxynucloside triphosphate(s), wherein the amplifying uses a portion of each template double-stranded nucleic acid as a template; and
  d. characterizing the single-stranded nucleic acid fragments and thereby characterizing the methylation state of at least portions of the target nucleic acids.

In another aspect, the present invention provides an isolated nucleic acid comprising:
(1) a nicking agent recognition sequence (NARS); and
(2) a double-stranded nucleic acid fragment that comprises:
  (a) if a target nucleic acid is single-stranded,
    (i) the target nucleic acid that has been treated and modified by a modifying agent that differentially modifies a nucleotide based on the methylation state of the nucleotide, and
    (ii) a nucleotide sequence that is completely complementary to the target nucleic acid that has been treated and modified by the modifying agent;
  wherein in the strand of said nucleic acid that contains the sense strand of the NARS, the sequence of the sense strand of the NARS is located 5' to nucleotide sequence (ii); or
  (b) if a target nucleic acid is double-stranded, the target nucleic acid that either said target nucleic acid or one strand thereof has been treated and modified by a modifying agent that differentially modifies a nucleotide based on the methylation state of the nucleotide,
  wherein in the strand of said nucleic acid that contains the sense strand of the NARS, the sequence of the sense strand of the NARS is located 5' to the nucleotide sequence of one strand of the target nucleic acid that has been treated and modified by the modifying agent.

In another aspect, the present invention provides a composition comprising:
  a. a single-stranded target nucleic acid that has been treated and modified by a modifying agent that modifies a nucleotide based on the methylation state of the nucleotide;
  b. a first oligonucleotide primer (ODNP) that comprises a sequence of a sense strand of a nicking agent recognition sequence (NARS) and a sequence that is at least substantially complementary to a first nucleotide sequence of the target nucleic acid; and
  c. a second ODNP that comprises a sequence that is at least substantially identical to a second nucleotide sequence of the target nucleic acid, wherein the second nucleotide sequence is located 5' to the first nucleotide sequence.

In a related aspect, the present invention provides a composition comprising:
  a. a double-stranded target nucleic acid that has been treated and modified by a modifying agent that modifies a nucleotide based on the methylation state of the nucleotide, the double-stranded target nucleic acid having a first strand and a second strand;
  b. a first oligonucleotide primer (ODNP) that comprises a sequence of a sense strand of a nicking agent recognition sequence (NARS) and a sequence that is at least substantially complementary to a first nucleotide sequence of the first strand of the target nucleic acid; and
  c. a second ODNP that comprises a sequence that is at least substantially complementary to a second nucleotide sequence of the second strand of the target nucleic acid, wherein the nucleotide sequence in the first strand of the target nucleic acid that corresponding to the second nucleotide sequence in the second strand of the target nucleic acid is located at 5' to the first nucleotide sequence in the first strand of the target nucleic acid.

BRIEF DESCRIPTION OF THE SEVERAL VIEWS OF THE DRAWINGS

FIGS. 5A–H are schematic diagrams of ligation products of exemplary adaptors and a target nucleic acid. The broken lines represent the target nucleic acid. The arrows above or below the TRERS (the abbreviation for "type IIs restriction endonuclease recognition sequence") indicate the directions from the TRERS to the cleavage site of a restriction endonuclease (RE) that recognizes the TRERS. Likewise, the arrows above or below the NERS (the abbreviation for "nicking endonuclease recognition sequence") indicate the directions from the NERS to the nicking site of a nicking endonuclease (NE) that recognizes the NERS.

DETAILED DESCRIPTION OF THE INVENTION

Figure 1:
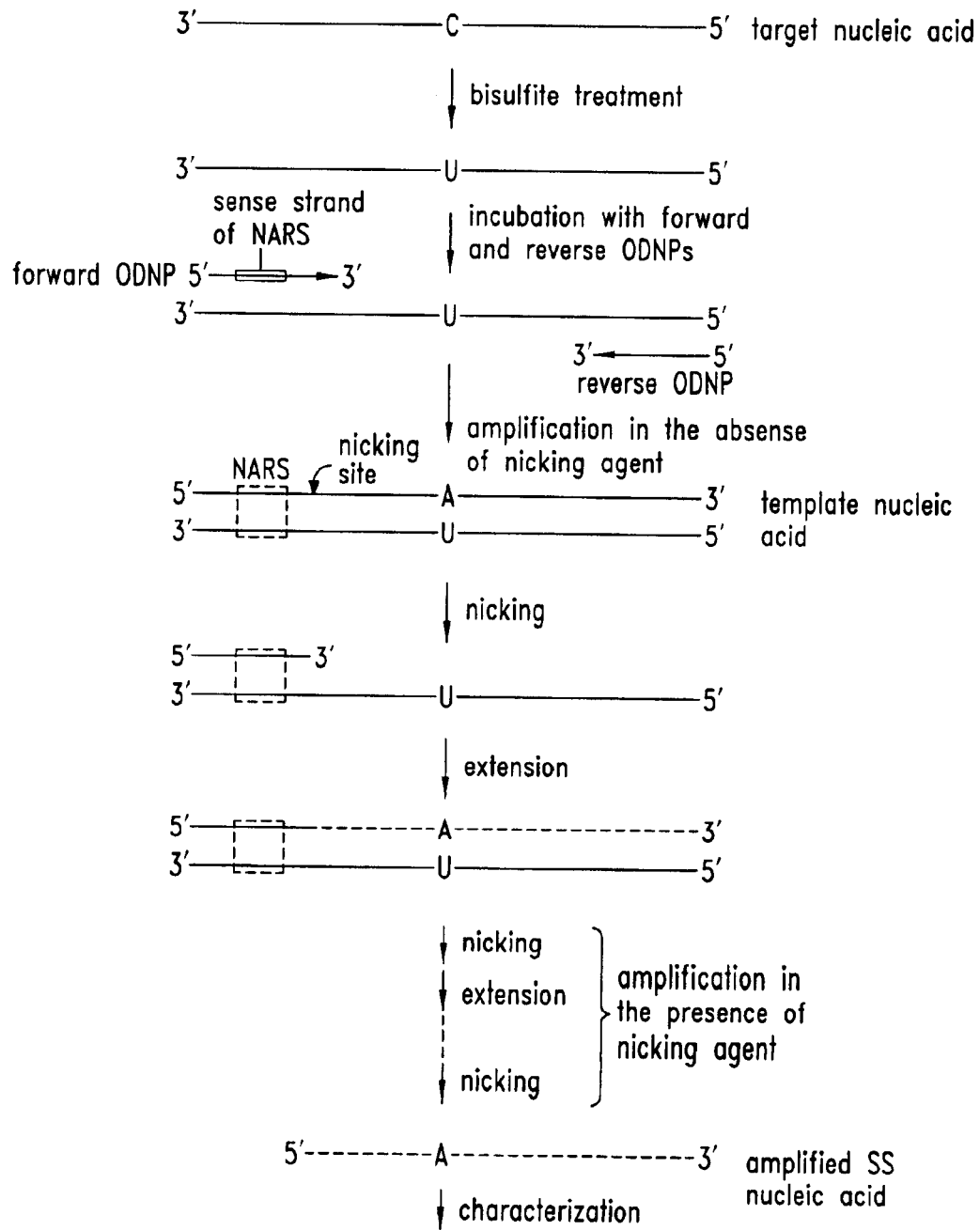
FIG. 1 is a schematic diagram of the major steps of an exemplary method for characterizing the nucleic acid methylation state of a target nucleic acid according to the present invention. In this diagram, bisulfite is used as a modifying agent, and the target nucleic acid contains an unmethylated cytosine at a defined position.

The present invention provides simple and efficient methods for characterizing nucleic acid methylation states using nicking agents. Prior to providing a detailed description of the present invention, it may be helpful to an understanding thereof to define conventions and provide definitions as used herein. Additional definitions are also provided throughout the description of the present invention.

A. Conventions/Definitions

The term "isolated nucleic acid molecule" refers to a double-stranded nucleic acid molecule that is not identical to any naturally occurring nucleic acid (e.g., a full-length genomic DNA molecule) and is not identical to any fragment of a naturally occurring genomic nucleic acid spanning more than three separate genes.

The terms "3'" and "5'" are used to describe the location of a particular site within a single strand of nucleic acid. When a location in a nucleic acid is "3' to" or "3' of" a reference nucleotide or a reference nucleotide sequence, this means that the location is between the 3' terminus of the reference nucleotide or the reference nucleotide sequence and the 3' hydroxyl of that strand of nucleic acid. Likewise, when a location in a nucleic acid is "5' to" or "5' of" a reference nucleotide or a reference nucleotide sequence, this means that the location is between the 5' terminus of the reference nucleotide or the reference nucleotide sequence and the 5' phosphate of that strand of nucleic acid. Further, when a nucleotide sequence is "directly 3' to" or "directly 3' of" a reference nucleotide or a reference nucleotide sequence, this means that the nucleotide sequence is directly adjacent to the 3' terminus of the reference nucleotide or the reference nucleotide sequence. Similarly, when a nucleotide sequence is "directly 5' to" or "directly 5' of" a reference nucleotide or a reference nucleotide sequence, this means that the nucleotide sequence is directly adjacent to the 5' terminus of the reference nucleotide or the reference nucleotide sequence.

As used herein, "nicking" refers to the cleavage of only one strand of a fully double-stranded nucleic acid molecule or a double-stranded portion of a partially double-stranded nucleic acid molecule at a specific position relative to a nucleotide sequence that is recognized by the enzyme that performs the nicking. The specific position where the nucleic acid is nicked is referred to as the "nicking site" (NS).

A "nicking agent" (NA) is an enzyme that recognizes a particular nucleotide sequence of a completely or partially double-stranded nucleic acid molecule and cleaves only one strand of the nucleic acid molecule at a specific position relative to the recognition sequence. Nicking agents include, but are not limited to, a nicking endonuclease (e g., N.BstNB I) and a restriction endonuclease (e.g., Hinc II) when a completely or partially double-stranded nucleic acid molecule contains a hemimodified recognition/cleavage sequence in which one strand contains at least one derivatized nucleotide(s) that prevents cleavage of that strand (i.e., the strand that contains the derivatized nucleotide(s)) by the restriction endonuclease.

A "nicking endonuclease" (NE), as used herein, refers to an endonuclease that recognizes a nucleotide sequence of a completely or partially double-stranded nucleic acid molecule and cleaves only one strand of the nucleic acid molecule at a specific location relative to the recognition sequence. Unlike a restriction endonuclease (RE), which requires its recognition sequence to be modified by containing at least one derivatized nucleotide to prevent cleavage of the derivatized nucleotide-containing strand of a fully or partially double-stranded nucleic acid molecule, a NE typically recognizes a nucleotide sequence composed of only native nucleotides and cleaves only one strand of a fully or partially double-stranded nucleic acid molecule that contains the nucleotide sequence.

As used herein, "native nucleotide" refers to adenylic acid, guanylic acid, cytidylic acid, thymidylic acid or uridylic acid. A "derivatized nucleotide" is a nucleotide other than a native nucleotide.

The nucleotide sequence of a completely or partially double-stranded nucleic acid molecule that a NA recognizes is referred to as the "nicking agent recognition sequence" (NARS). Likewise, the nucleotide sequence of a completely or partially double-stranded nucleic acid molecule that a NE recognizes is referred to as the "nicking endonuclease recognition sequence" (NERS). The specific sequence that a RE recognizes is referred to as the "restriction endonuclease recognition sequence" (RERS). A "hemimodified RERS," as used herein, refers to a double-stranded RERS in which one strand of the recognition sequence contains at least one derivatized nucleotide (e.g., a-thio deoxynucleotide) that prevents cleavage of that strand (i.e., the strand that contains the derivatized nucleotide within the recognition sequence) by a RE that recognizes the RERS.

In certain embodiments, a NARS is a double-stranded nucleotide sequence where each nucleotide in one strand of the sequence is complementary to the nucleotide at its corresponding position in the other strand. In such embodiments, the sequence of a NARS in the strand containing a NS nickable by a NA that recognizes the NARS is referred to as a "sequence of the sense strand of the NARS" or a "sequence of the sense strand of the double-stranded NARS," while the sequence of the NARS in the strand that does not contain the NS is referred to as a "sequence of the antisense strand of the NARS" or a "sequence of the antisense strand of the double-stranded NARS."

Likewise, in the embodiments where a NERS is a double-stranded nucleotide sequence of which one strand is exactly complementary to the other strand, the sequence of a NERS located in the strand containing a NS nickable by a NE that recognizes the NERS is referred to as a "sequence of a sense strand of the NERS" or a "sequence of the sense strand of the double-stranded NERS," while the sequence of the NERS located in the strand that does not contain the NS is referred to a "sequence of the antisense strand of the NERS" or a "sequence of the antisense strand of the double-stranded NERS." For example, the recognition sequence and the nicking site of an exemplary nicking endonuclease, N.BstNB I, are shown below with "▼" to indicate the cleavage site and N to indicate any nucleotide:

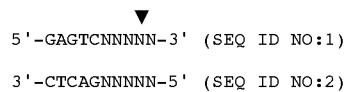

5'-GAGTCNNNNN-3' (SEQ ID NO:1)

3'-CTCAGNNNNN-5' (SEQ ID NO:2)

The sequence of the sense strand of the N.BstNB I recognition sequence is 5'-GAGTC-3', whereas that of the antisense strand is 5'-GACTC-3'.

Similarly, the sequence of a hemimodified RERS in the strand containing a NS nickable by a RE that recognizes the hemimodified RERS (i.e., the strand that does not contain any derivatized nucleotides) is referred to as "the sequence of the sense strand of the hemimodified RERS" and is located in "the sense strand of the hemimodified RERS" of a hemimodified RERS-containing nucleic acid, while the sequence of the hemimodified RERS in the strand that does not contain the NS (i.e., the strand that contains derivatized nucleotide(s)) is referred to as "the sequence of the antisense strand of the hemimodified RERS" and is located in "the antisense strand of the hemimodified RERS" of a hemimodified RERS-containing nucleic acid.

In certain other embodiments, a NARS is an at most partially double-stranded nucleotide sequence that has one or more nucleotide mismatches, but contains an intact sense strand of a double-stranded NARS as described above. According to the convention used herein, in the context of describing a NARS, when two nucleic acid molecules anneal to one another so as to form a hybridized product, and the hybridized product includes a NARS, and there is at least one mismatched base pair within the NARS of the hybridized product, then this NARS is considered to be only partially double-stranded. Such NARSs may be recognized by certain nicking agents (e.g., N.BstNB I) that require only one strand of double-stranded recognition sequences for their nicking activities. For instance, the NARS of N.BstNB I may contain, in certain embodiments, an intact sense strand, as follows,

5'-GAGTC-3'

3'-NNNNN-5' where N indicates any nucleotide, and N at one position may or may not be identical to N at another position, however there is at least one mismatched base pair within this recognition sequence. In this situation, the NARS will be characterized as having at least one mismatched nucleotide.

In certain other embodiments, a NARS is a partially or completely single-stranded nucleotide sequence that has one or more unmatched nucleotides, but contains an intact sense strand of a double-stranded NARS as described above. According to the convention used herein, in the context of describing a NARS, when two nucleic acid molecules (i.e., a first and a second strand) anneal to one another so as to form a hybridized product, and the hybridized product includes a nucleotide sequence in the first strand that is recognized by a NA, i.e., the hybridized product contains a NARS, and at least one nucleotide in the sequence recognized by the NA does not correspond to, i.e., is not across from, a nucleotide in the second strand when the hybridized product is formed, then there is at least one unmatched nucleotide within the NARS of the hybridized product, and this NARS is considered to be partially or completely single-stranded. Such NARSs may be recognized by certain nicking agents (e.g., N.BstNB I) that require only one strand of double-stranded recognition sequences for their nicking activities. For instance, the NARS of N.BstNB I may contain, in certain embodiments, an intact sense strand, as follows,

5'-GAGTC-3'

3'-N$_{0-4}$-5'

(where "N" indicates any nucleotide, 0–4 indicates the number of the nucleotides "N," a "N" at one position may or may not be identical to a "N" at another position), which contains the sequence of the sense strand of the double-stranded recognition sequence of N.BstNB I. In this instance, at least one of G, A, G, T or C is unmatched, in that there is no corresponding nucleotide in the complementary strand. This situation arises, e.g., when there is a "loop" in the hybridized product, and particularly when the sense sequence is present, completely or in part, within a loop.

The phrase "amplifying a nucleic acid molecule" or "amplification of a nucleic acid molecule" refers to the making of two or more copies of the particular nucleic acid molecule. "Amplifying a single-stranded nucleic acid" refers to making multiple single-stranded nucleic acid molecules that each have the same number of nucleotide bases and the same sequence of nucleotide bases.

A first nucleic acid molecule is "derived from" or is a "derivative of" a second nucleic acid molecule if the first nucleic acid is a primer extension product (or an amplification product) using a portion of the second nucleic acid molecule modified by a modifying agent (or the complement of the second nucleic acid modified by a modifying agent) as a template.

A first nucleotide sequence is "at least substantially identical" to a second nucleotide sequence when a nucleic acid molecule comprising the complement of the first sequence (1) is able to anneal to a nucleic acid molecule comprising the second nucleotide sequence under at least one set of conditions (e.g., nucleic acid amplification reaction conditions) and (2) can function as a primer in a primer extension reaction using the nucleic acid molecule comprising the second sequence as a template. In certain embodiments, the first sequence is exactly identical to the second sequence, that is, each nucleotide of the first sequence at each position is identical to the nucleotide of the second sequence at the same position.

A first nucleotide sequence is "at least substantially complementary" to a second nucleotide sequence when a nucleic acid molecule comprising the first sequence (1) is able to anneal to a nucleic acid molecule comprising the second sequence under at least one set of conditions (e.g., nucleic acid amplification reaction conditions), and (2) can function as a primer for a primer extension reaction using a nucleic acid molecule comprising the second sequence as a template. In certain embodiments, the first sequence is exactly complementary to the second sequence, that is, each nucleotide of the first sequence is complementary to the nucleotide of the second sequence at its corresponding position.

A nucleotide in the first strand of a double-stranded nucleic acid molecule that is located at a position "corresponding to" a position (e.g., a defined position) in the second strand of the molecule refers to the nucleotide in the first strand that is complementary to the nucleotide at the corresponding position in the second strand. Likewise, a position in the first strand of a double-stranded nucleic acid molecule "corresponding to" a nicking site within the second strand of the molecule refers to the position between the two nucleotides in the first strand that are complementary to the nucleotides in the second strand that surround the nicking site.

A "type IIS restriction endonuclease" is a restriction endonuclease that recognizes an asymmetric recognition sequence and cleaves outside its recognition sequence. Exemplary type IIs restriction endonucleases include BpmI, BsgI, Eco57 I, and Fok I.

A "modifying agent" is a chemical compound or composition that differentially modifies a nucleotide based on the methylation state of the nucleotide, i.e., whether the nucleotide does or does not have a methyl substituent, so that the resulting modified nucleotide has a base-pairing preference different from the original, unmodified nucleotide. An exemplary modifying agent is sodium sulfite. Sodium sulfite modifies unmethylated cytosine (where cytosine does not have a methyl group) to produce uracil, but does not modify methylated cytosine. The resulting uracil preferentially base pairs with adenine rather than the guanine, where unmethylated cytosine preferentially base pairs with guanine rather than adenine.

"Treating a target nucleic acid with a modifying agent" refers to the action of combining the target nucleic acid with a modifying agent under conditions such that a nucleotide sensitive to the modifying agent in the target nucleic acid would be converted to a nucleotide (a "modified nucleotide") having a base-pairing preference different from the unmodified nucleotide. If the modifying agent is specific to single-stranded nucleic acid (i.e., the modifying agent can only modify a single-stranded nucleic acid), but a target nucleic acid is double-stranded, then "treating a target nucleic acid" includes the step of denaturing the double-stranded molecule to provide single-stranded molecules. With sodium sulfite as an exemplary modifying agent, treating a target nucleic acid with a modifying agent refers to the combination of the target nucleic acid (if single-stranded) or the denaturation products thereof (if double-stranded) and sodium sulfite under conditions that unmethylated cytosine(s), if present in the target nucleic acid, are converted to uracil.

A "treated" nucleotide refers to a nucleotide that has been exposed to a modifying agent under conditions that could provide for differential modification of a nucleotide based on its methylation state. If the nucleotide that will be "treated" has a methylation state that is not modifiable by the modifying agent, the treated nucleotide remains the same as the untreated nucleotide. However, if the nucleotide that will be treated has a methylation state that is modifiable by the modifying agent, then treating causes the treated nucleotide to be different from the untreated nucleotide. Such a treated nucleotide (i.e., a nucleotide converted from another nucleotide that has been treated by a modifying agent) is referred to as a "modified" nucleotide. For instance, when a methylated cytosine is treated by bisulfite, it remains unchanged. This methylated cytosine can be referred to as a "treated" nucleotide, but not as a "modified" nucleotide. On the other hand, when an unmethylated cytosine is treated by bisulfite so as to form uracil, the resulting uracil can be referred to as both a "treated" nucleotide and as a "modified" nucleotide. Similarly, a "treated" nucleic acid refers to a nucleic acid that has been exposed to a modifying agent under conditions that could cause one or more nucleotides of the nucleic acid to convert to a modified form. A "modified" nucleic acid refers to a nucleic acid that comprises at least one "modified" nucleotide.

A "methylation state" of a nucleotide refers to whether the nucleotide is methylated or unmethylated. A "methylation state" of a nucleic acid refers to (1) whether a nucleotide at a defined position in the nucleic acid is methylated or unmethylated; or (2) the methylation level of the nucleic acid (or a region thereof). The "methylation level" of a nucleic acid (or a region thereof) refers to the ratio of the number of a particular type of nucleotide (e.g., cytosine) that has been methylated to the total number of the particular type of nucleotide (including methylated and unmethylated nucleotides) in the nucleic acid (or a region thereof).

"Characterizing the methylation state of a nucleic acid" refers to obtaining information that describes the methylation state of the nucleic acid. More specifically, it refers to obtaining information about the methylation state of at least one nucleotide at a position of interest, or obtaining information about the methylation level of a nucleic acid. In certain embodiments, the methylation state of each nucleotide within a region of interest in a nucleic acid is obtained.

A primer pair that is "specific to one strand" of a modified double-stranded nucleic acid molecule refers to a pair of primers that, under appropriate conditions, function as primers for amplifying a nucleic acid fragment using only one strand of the modified double-stranded nucleic acid as a template. A primer pair that is "not specific to one strand" of a modified double-stranded nucleic acid refers to a pair of primers that function as primers for amplifying a nucleic acid fragment using both strands of the modified double-stranded nucleic acid as a template.

A "nucleic acid fragment encompassing a first ODNP and a second ODNP" refers to a double-stranded nucleic acid fragment wherein one strand consists of the sequence of the first ODNP, the sequence complementary to the sequence of the second ODNP, and a nucleotide sequence located between the first ODNP and the complement of the second ODNP; while the other strand consists of the sequence complementary to the sequence of the first ODNP, the sequence of the second ODNP, and a nucleotide sequence located between the complement of the first ODNP and the sequence of the second ODNP.

B. Methods for Nucleic Acid Methylation Analysis

In one aspect, the present invention provides methods for characterizing the methylation state of at least a portion of a single-stranded target nucleic acid. The methods comprise the following steps: (1) treating a target nucleic acid with a modifying agent that differently modifies a nucleotide based on the methylation state of the nucleotide to provide a treated target nucleic acid; (2) providing a template double-stranded nucleic acid that comprises a nicking agent recognition sequence (NARS) and a portion of the treated target nucleic acid or an amplification product of the portion of the modified target nucleic acid; (3) amplifying a single-stranded nucleic acid fragment in the presence of a nicking agent (NA) that recognizes the NARS, a DNA polymerase, and one or more deoxynucleoside triphosphate(s), using at least a portion of the template double-stranded nucleic acid as a template; and (4) characterizing the single-stranded nucleic acid fragment to thereby characterize the methylation state of at least a portion of the single-stranded target nucleic acid. The second step may be accomplished by the use of an oligonucleotide primer (ODNP) pair where one primer comprises a sequence of a sense strand of a NARS. Alternatively, the second step may be accomplished by the use of an adaptor comprising a double-stranded NARS.

Figure 2:
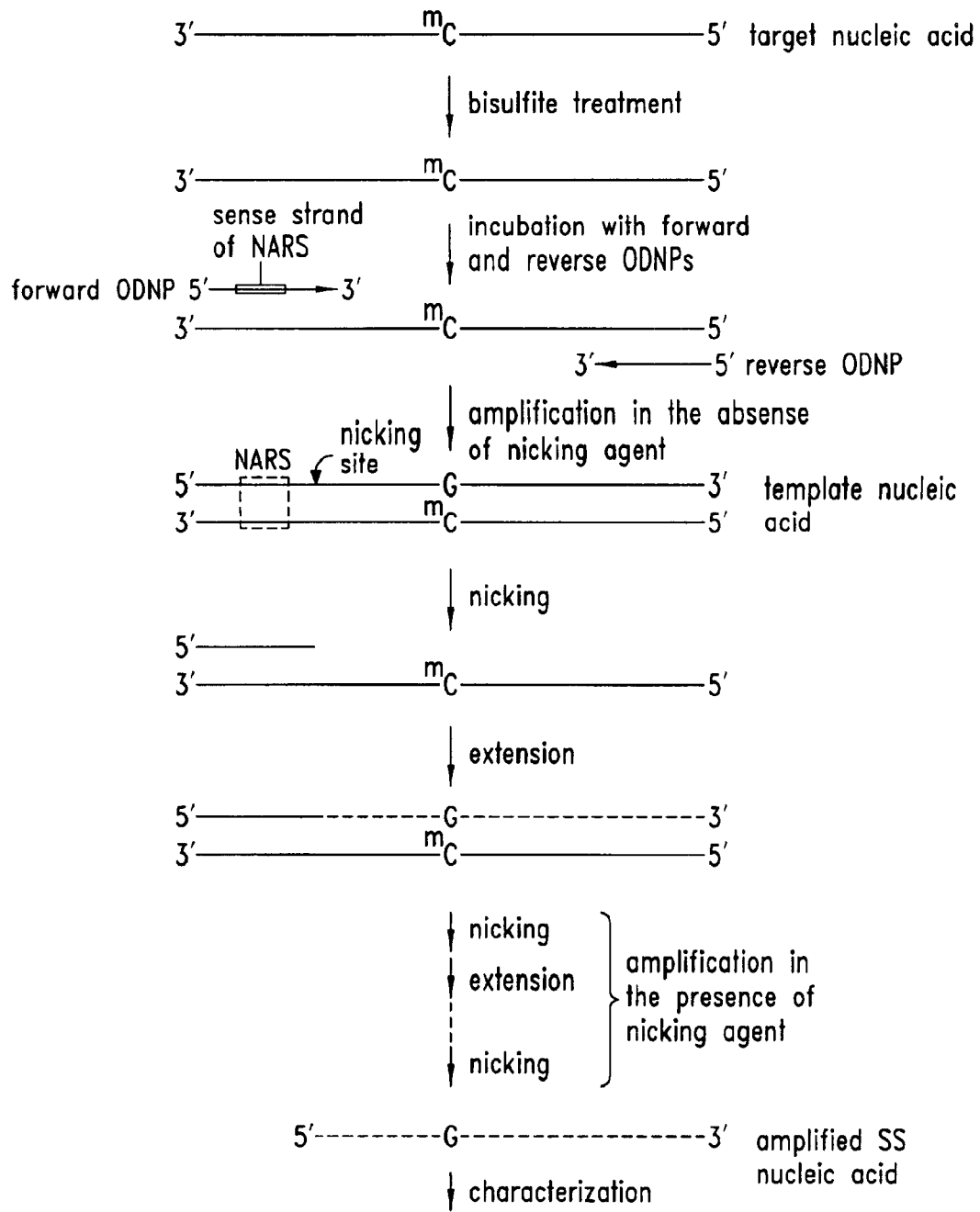
FIG. 2 is a schematic diagram of the major steps of another exemplary method for characterizing the nucleic acid methylation state of a target nucleic acid according to the present invention. In this diagram, bisulfite is used as a modifying agent, and the target nucleic acid contains a methylated cytosine at a defined position.

An exemplary embodiment of the present invention is illustrated in FIGS. 1 and 2. In this embodiment, sodium bisulfite is used as the modifying agent, a NA that nicks outside its recognition sequence is used as the nicking agent, a single-stranded nucleic acid is used as the target nucleic acid, and an ODNP pair are used to make a double-stranded template nucleic acid that comprises a NARS and at least a portion of the target nucleic acid. As illustrated in FIG. 1, if a target nucleic acid contains an unmethylated cytosine at a defined position, bisulfite treatment of the target nucleic acid modifies the unmethylated cytosine to a uracil. The resulting modified target nucleic acid is then used as a template for preparing a double-stranded nucleic acid that comprises both a NARS and at least a portion of the modified target nucleic acid that contains the uracil, using an ODNP pair. One ODNP in the pair ("first ODNP" or "forward ODNP") comprises a sequence of a sense strand of a NARS and a nucleotide sequence at least substantially complementary to a nucleotide sequence of the target nucleic acid ("first nucleotide sequence" of the target nucleic acid) located 3' to the uracil. The other ODNP in the pair ("second ODNP" or "reverse ODNP") comprises a nucleotide sequence at least substantially identical to a second nucleotide sequence of the target nucleic acid located 5' to the uracil. In the presence of a DNA polymerase ("first DNA polymerase") and deoxyribonucleoside triphosphates, the forward ODNP extends from its 3' terminus using the modified target nucleic acid as a template to produce a complementary strand of the modified target nucleic acid that incorporates an adenine at the position corresponding to the uracil. After denaturation, the reverse ODNP then anneals to the complementary strand of the modified target nucleic acid and extends from its 3' terminus to produce an extension product that incorporates the sequence of the antisense strand of the NARS. The resulting fully or partially double-stranded nucleic acid thus comprises a double-stranded NARS and at least a portion of the modified target nucleic acid that contains the uracil and the complementary sequence of the portion of the modified target nucleic acid. The denaturation and extension may be repeated multiple times to amplify the above double-stranded nucleic acid. However, as described in details below, a portion of one strand of the double-stranded nucleic acid will be further amplified in the presence of a NA that recognizes the NARS. Thus, although amplification of the double-stranded nucleic acid may be carried out, it is not required. Because this double-stranded nucleic acid is used as a template for amplifying a single-stranded nucleic acid, as described below, it is referred to as a "template nucleic acid."

The above template nucleic acid may be nicked by a NA that recognizes the NARS, producing a 3' terminus and a 5' terminus at the nicking site. If the fragment containing the 5' terminus at the nicking site is relatively short (e.g., less than 17 nucleotides in length), it may dissociate from the other portion of the double-stranded nucleic acid under certain reaction conditions (e.g., at 60° C.). However, if this fragment does not readily dissociate, it may be displaced by the extension from 3' terminus at the nicking site in the presence of the first DNA polymerase that is 5'→3' exonuclease deficient and has a strand displacement activity. Stand displacement may also occur in the absence of the strand displacement activity of a first DNA polymerase, but in the presence of a strand displacement facilitator. However, if the first DNA polymerase has a 5'→3' exonuclease activity, unless the fragment containing the 5' terminus at the nicking site readily dissociates from the other portion of the double-stranded nucleic acid, it needs to be inactivated, and a second DNA polymerase that is 5'→3' exonuclease deficient may be added to preserve the fragment containing the 5' terminus at the nicking site. The above nicking-extension cycles can be repeated multiple times, resulting in the accumulation/amplification of the fragment containing the 5' terminus at the nicking site. Such an amplified fragment contains an adenine at the defined position corresponding to the original unmethylated cytosine in the target nucleic acid. By characterizing the amplified fragment and determining the identity of the nucleotide in the amplified fragment (i.e., an adenine) at the position corresponding to the defined position in the target nucleic acid, one may determine that the cytosine at the defined position in the target nucleic acid is unmethylated.

A similar process is illustrated in FIG. 2 where a target nucleic acid contains a methylated cytosine, instead of an unmethylated cytosine as illustrated in FIG. 1, at a defined position. Because bisulfite treatment does not convert the methylated cytosine to another nucleotide, and because the methylated cytosine forms a base pair with a guanosine, the amplified single-stranded nucleic acid in the presence of a nicking agent and a DNA polymerase contains a guanosine at the position corresponding to the defined position in the target nucleic acid. By characterizing the amplified fragment and determining the identity of the nucleotide in the amplified fragment (i.e., a guanosine) at the position corresponding to the defined position in the target nucleic acid, one may determine that the cytosine at the defined position in the target nucleic acid is methylated.

In certain embodiments, when a target nucleic acid comprises a sequence of the antisense strand of a NARS located 3' to a nucleotide, or a portion, of a target nucleic acid of which methylation state is of interest, only one ODNP is needed to prepare a template nucleic acid. The ODNP need be at least substantially complementary to the portion of the target nucleic acid that comprises the sequence of the antisense strand of the NARS. In addition, the ODNP comprises the sequence of the sense strand of the NARS to form base pairs with the sequence of the antisense strand of the NARS in the target when the ODNP anneals to the target. The extension of the ODNP using the treated target nucleic acid as a template and subsequent nicking of the extension product produces a single-stranded nucleic acid that comprises the complement of the nucleotide or the portion of the target of which methylation state is of interest. The repetition of the above extension and nicking process amplifies the above single-stranded nucleic acid. This amplified single-stranded nucleic acid may be characterized and thus the methylation state of the nucleotide or the portion of the target of interest may be determined.

In other embodiments, even when a target nucleic acid does not comprise a sequence of the antisense strand of a NARS located 3' to a nucleotide, or a portion, of a target nucleic acid of which methylation state is of interest, it is still possible to use only one ODNP to prepare a template nucleic acid. The ODNP need be at least substantially complementary to a portion of the target located 3' to the nucleotide, or the portion, of the target of which methylation state is of interest. In addition, the ODNP comprises a sequence of the sense strand of a NARS. As described above, certain nicking agents (e.g., N.BstNB I) are capable of nicking a substrate nucleic acid that comprise only sequences of the sense strands of their double-stranded recognition sequences. Thus, the extension product of the ODNP using the target as a template may be nicked by a nicking agent that recognizes the sequence of the sense strand of the NARS in the ODNP. The resulting nicked product may be extended from the 3' terminus at the nicking site. The above extension-nicking cycle may be repeated multiple times, resulting in the amplification of a single-stranded nucleic acid that comprises the complement of the nucleotide, or the portion, of the target nucleic acid of which methylation state is of interest. The characterization of this amplified single-stranded nucleic acid may indicate the methylation state of the nucleotide, or the portion, of the target nucleic acid of interest.

When a target nucleic acid is double-stranded, the characterization of its methylation state becomes more complicated. The complication is derived from the fact that the nucleic acid strands may no longer be complementary after being treated with a modifying agent. One way to simplify the complication is to denature a double-stranded target nucleic acid into two single strands and subsequently separate one strand from the other. For instance, after denaturation, one strand of the target nucleic acid may anneal to an immobilized single-stranded nucleic acid that is complementary to that strand of the target nucleic acid to form an immobilized duplex. The immobilized duplex may be washed to remove the other strand of the target nucleic acid and subsequently denatured to release the strand of the target nucleic acid that anneals to the immobilized single-stranded nucleic acid. The characterization of the methylation state of the released strand will be the same as that of a single-stranded target nucleic acid as described herein.

Another way to simplify the complication associated with a double-stranded target nucleic acid is to use only one ODNP that comprises a sequence of the sense strand of a NARS and is at least substantially complementary to the one strand of the double-stranded target located 3' to the nucleotide, or the portion, of the target of which methylation state is of interest. If both strands contain nucleotides or portions of which methylation state is of interest, two ODNPs as described above may be used. However, each ODNP is mixed with the target after being treated with a modifying agent in the absence of the other ODNP to prevent amplification of nucleic acids encompassing both ODNPs.

An alternative way to simplify the complication associated with a double-stranded target nucleic acid is to use strand-specific primers to analyze each strand separately. Strand-specific primer pairs are designed to anneal to regions rich in nucleotides that may be differentially modified by the treatment of the modifying agent. See, Frommer et al., *Proc. Natl. Acad. Sci. USA* 89: 1827–31, 1992; Herman et al., *Proc. Natl. Acad. Sci.* 93: 9821–6, 1996. For instance, when the modifying agent is sodium bisulfite, a region with a high density of CpG dinucleotides (e.g., a region in CpG islands) may be used for designing strand-specific primer pairs. Because a strand-specific primer pair amplifies a nucleic acid fragment using only one strand of a double-stranded target nucleic acid as a template, the process of characterizing the methylation state of that strand of the double-stranded target nucleic acid is similar to that of a single-stranded target nucleic acid.

Alternatively, a primer pair that is not specific to one strand of a double-stranded target nucleic acid may be used to provide or amplify a double-stranded template nucleic acid fragment that comprises a region within which the methylation state of a nucleotide (or nucleotides) is of interest. Because after the treatment by a modifying agent, the two strands of the double-stranded target nucleic acid are no longer complementary, the amplification products using a primer pair that is not specific to one strand of the treated target nucleic acid are a mixture of amplified fragments using each of the two strands of the treated double-stranded target nucleic acid as a template.

Figure 3A:
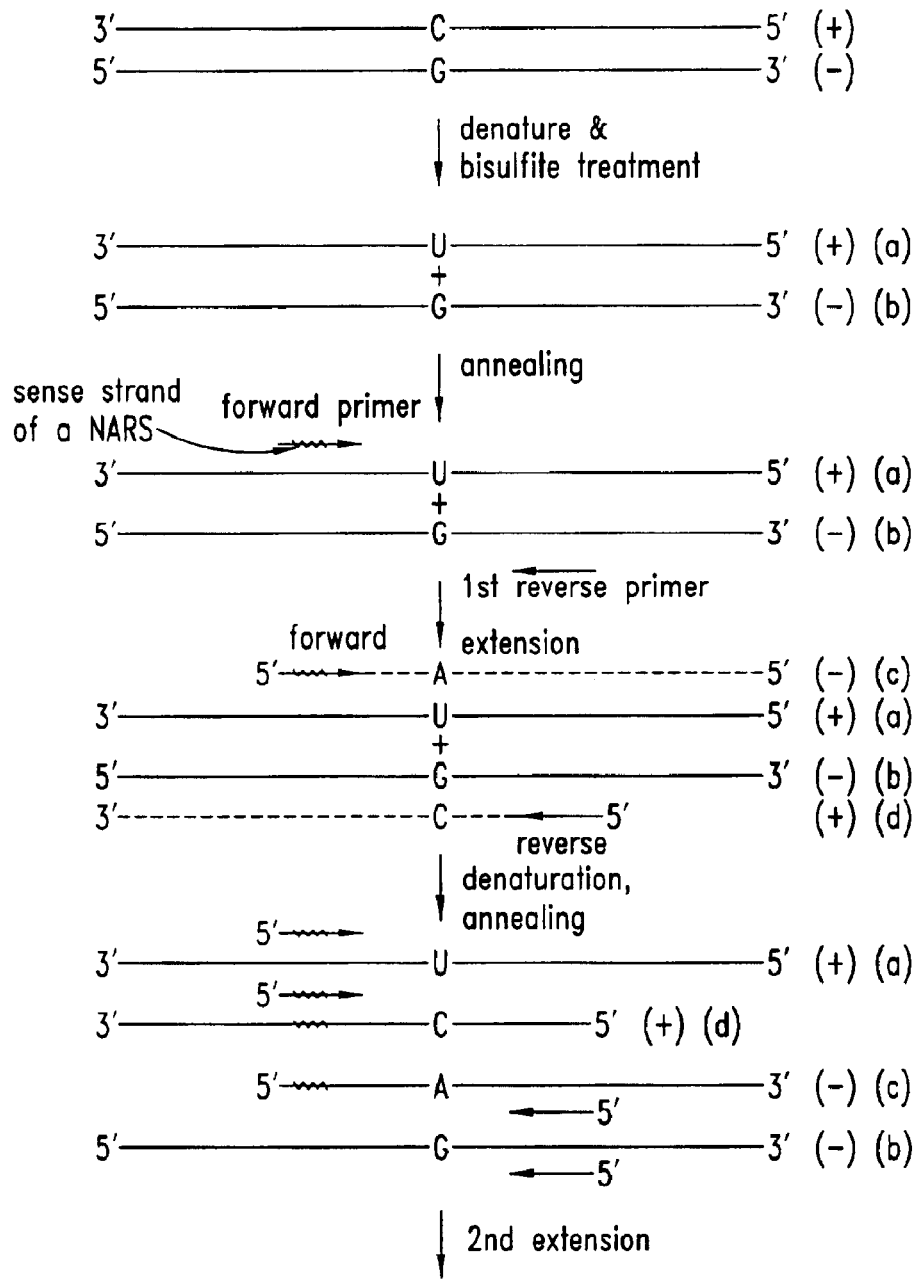
FIGS. 3A and 3B are schematic diagrams of the process of making a double-stranded template nucleic acid that comprises a nicking agent recognition sequence (NARS) and a portion of a target nucleic acid or a derivative thereof. In this diagram, bisulfite is used as a modifying agent, the target nucleic acid has an unmethylated cytosine at a defined position, and a primer pair is used that is not specific to only one strand of the target nucleic acid treated by the modifying agent.
Figure 3B:
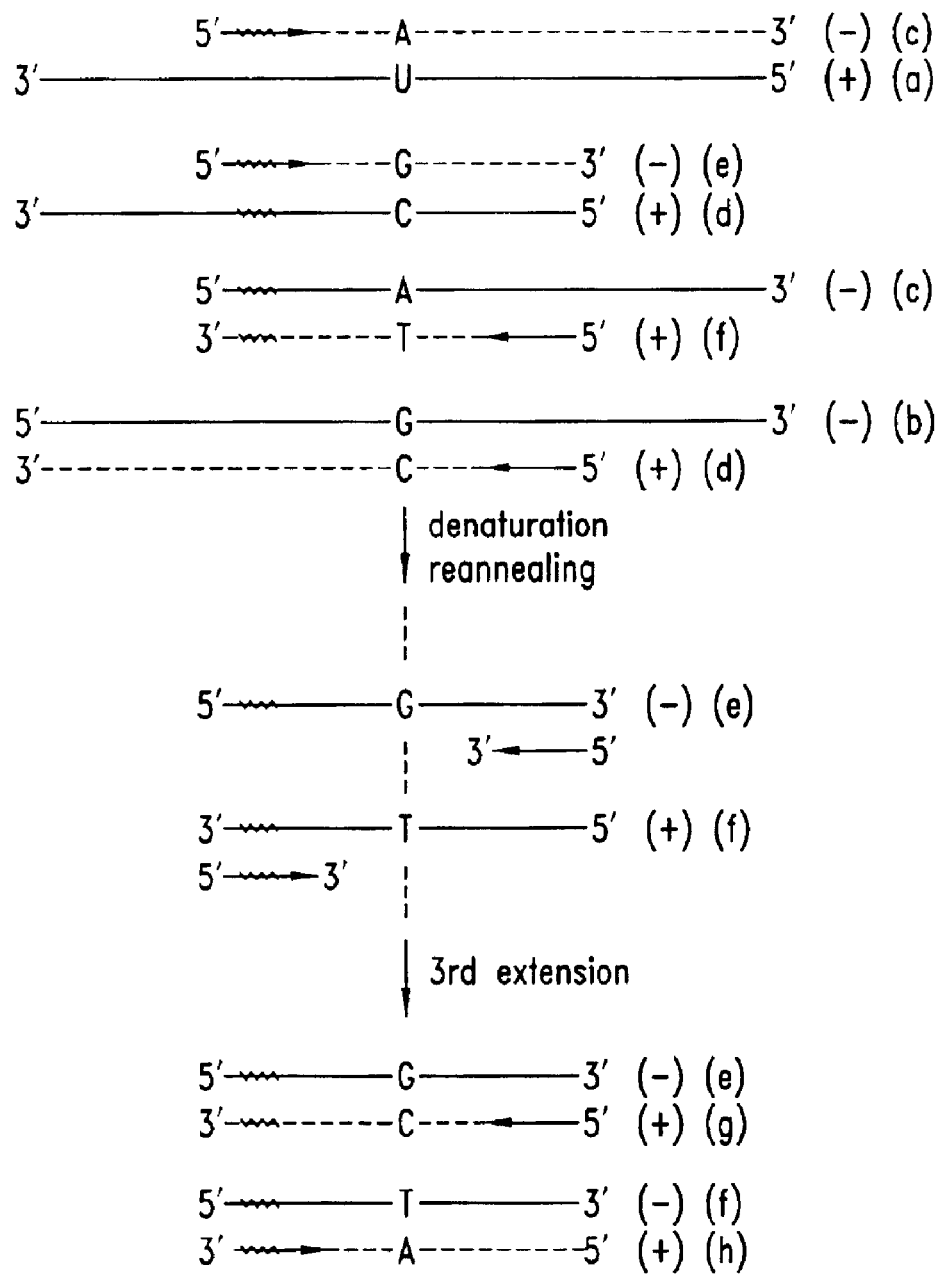

A detailed description of the above process is illustrated in FIG. 3A using sodium bisulfite as an exemplary modifying agent. Referring to FIG. 3A, a double-stranded target nucleic acid contains a C at a defined position in one strand ("(+) strand") and a G at a position corresponding to the defined position in the other strand ("(−) strand"). After the denaturation and sodium bisulfite treatment, the C at the defined position in the (+) strand is converted to a U, while the G at a position corresponding to the defied position in the (−) strand remains the same. The (+) strand of the treated target nucleic acid is referred to as the (a) strand, whereas the (−) strand of the treated target nucleic acid is referred to as the (b) strand. In the presence of a primer pair that are not specific to either (a) or (b) strand, the forward primer that comprises a sequence of a sense strand of a NARS (represented by a waived line) anneals to the (a) strand, and the reverse primer anneals to the (b) strand. In the presence of a DNA polymerase, both the forward reverse primers are extended. The resulting extension products from the forward and reverse primers are referred to as the (c) strand and the (d) strand, respectively. Upon the separation of the extension products from their corresponding templates, the forward primer may then anneal to either the (a) strand (which has a U at the defined position) or the (d) strand (which has a C at the position identical to the defined position). Likewise, the reverse primer may then anneal to either the (b) strand (which has a G at the position corresponding to the defined position) or the (c) strand (which has an A at the position corresponding to the defined position). Thus, a second extension reaction produces two extension products in addition to the (c) strand and the (d) strand: an extension product (the (e) strand) from the forward primer using the (d) strand as a template, and an extension product (the (f) strand) from the reverse primer using the (c) strand as a template (FIG. 3B). The (e) strand has a G at the position corresponding to the defined position, whereas the (f) strand has a T at the position identical to the defined position. The (e) strand and the (f) strand will in turn function as a template for the reverse primer and the forward primer, respectively, to provide extension products the (g) strand and the (h) strand. Thus, two kinds of extension/amplification products are produced that encompass the forward primer and the reverse primer: One is a double-stranded nucleic acid fragment consisting of the (e) strand and the (g) strand; and the other is a double-stranded nucleic acid fragment consisting of the (f) strand and the (h) strand. The former extension/amplification product contains a C–G base pair at the positions of interest while the latter contains an A–T base pair at the positions of interest. The presence of the latter extension/amplification product detected by subsequent characterization of a single-stranded nucleic acid fragment amplified using the extension product as a template indicates that the C at the defined position of the target double-stranded nucleic acid is unmethylated.

Figure 4:
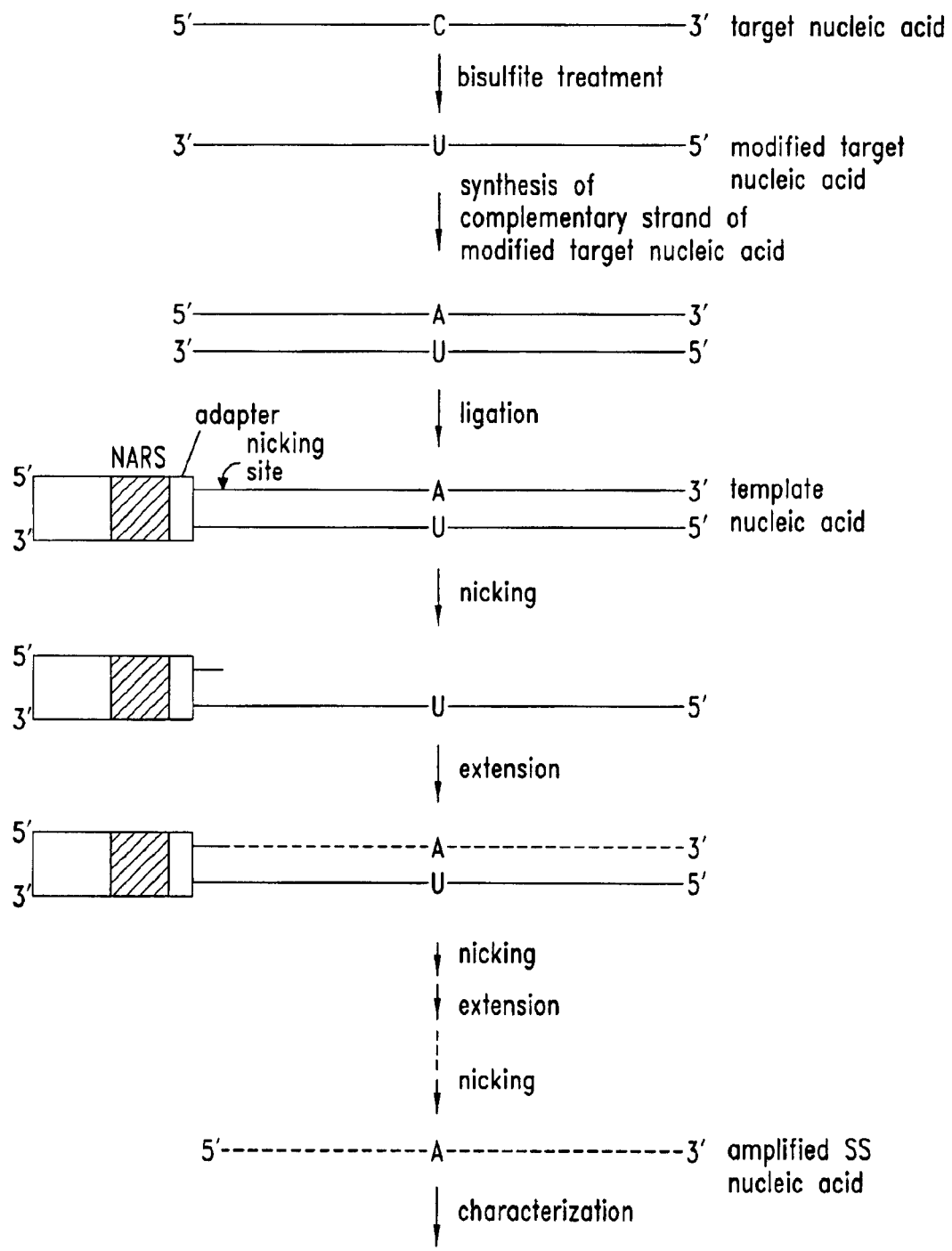
FIG. 4 is a schematic diagram of another exemplary method for characterizing the nucleic acid methylation state of a target nucleic acid according to the present invention. In this diagram, bisulfite is used as a modifying agent, the target nucleic acid has an unmethylated cytosine, and an adaptor that comprises a nicking agent recognition sequence is used to provide a template nucleic acid for amplifying a single-stranded nucleic acid fragment.

An alternative way of providing a double-stranded template nucleic acid is to use a nucleic acid adaptor that comprises a NARS. An exemplary embodiment is illustrated in FIG. 4 where sodium bisulfite is used as a modifying agent, a NA that nicks outside its recognition sequence is used as a nicking agent, and a single-stranded nucleic acid is used as a target nucleic acid. As illustrated in FIG. 4, the cytosine at a defined position in the target nucleic acid is unmethylated and is subsequently converted to a uracil by bisulfite treatment. The resulting modified target nucleic acid is then used as a template to synthesize its complementary strand in which an adenine forms a base pair with the uracil at the defined position in the modified target nucleic acid and thus provide a double-stranded nucleic acid. This double-stranded nucleic acid may then be ligated to a nucleic acid adaptor that comprises a double-stranded NARS to produce a template nucleic acid for amplifying a single-stranded nucleic acid in the presence of a nicking agent that recognizes the NARS and a DNA polymerase. The amplified single-stranded nucleic acid contains an adenine at the position corresponding to the defined position in the target nucleic acid. By characterizing the amplified fragment and determining the identity of the nucleotide in the amplified fragment (i.e., an adenine) at the position corresponding to the defined position in the target nucleic acid, one may determine that the cytosine at the defined position in the target nucleic acid is unmethylated.

On the other hand, if the target nucleic acid contains a methylated cytosine, bisulfite treatment does not convert this nucleotide to another nucleotide. Thus, the amplified single-stranded nucleic acid contains a guanosine at the position corresponding to the defined position in the target nucleic acid. By characterizing the amplified fragment and determining the identity of the nucleotide in the amplified fragment (i.e., a guanosine) at the position corresponding to the defined position in the target nucleic acid, one may determine that the cytosine at the defined position in the target nucleic acid is methylated.

When a target nucleic acid is double-stranded, after being treated with a modifying agent, the two nucleic acid strands may no longer be complementary with each other. Depending on the methylation state of which strand is of interest, the treated double-stranded target nucleic acid may be ligated to a nucleic acid adaptor so that the strand of which the methylation state is of interest is used as a template for amplifying a single-stranded nucleic acid fragment. The subsequent characterization of the amplified single-stranded nucleic acid allows the determination of the methylation state of that strand of the target nucleic acid.

1. Modification of Target Nucleic Acids

As described above, a target nucleic acid is first treated with a modifying agent for characterizing its methylation state. The target nucleic acid of the present invention may be any nucleic acid molecule of which the methylation state is of interest. It may be single-stranded or double-stranded. It may be immobilized to a solid support via its 5' or 3' terminus if the target nucleic acid is single-stranded, via its 5' or 3' terminus of one strand if the target nucleic acid is double-stranded, or via another region of the target. If the target nucleic acid is single-stranded, it may or may not be one strand of a denatured double-stranded nucleic acid.

The target nucleic acid of the present invention may be originated from a naturally occurring biological sample, or from a genetically engineered biological sample. In certain preferred embodiments, the target nucleic acid is originated from a diseased tissue or organ, such as a tumor tissue.

In certain embodiments where it may be desirable to synthesize a relatively short single-stranded nucleic acid, the target nucleic acid may be first subject to enzymatic, chemical, or mechanic cleavages. Enzymatic cleavages may be accomplished, for example, by digesting the nucleic acid molecule with a restriction endonuclease that recognizes a specific sequence within the target nucleic acid. Alternatively, enzymatic cleavages may be accomplished by nicking the target nucleic acid with a nicking agent that recognizes a specific sequence within the nucleic acid molecule. Enzymatic cleavages may also be oligonucleotide-directed cleavages according to Szybalski (U.S. Pat. No. 4,935,357). Chemical and mechanic cleavages may be accomplished by any method known in the art suitable for cleaving nucleic acid molecules such as shearing.

The modifying agent of the present invention may be any chemical compound or composition that differentially modifies a nucleotide based on the methylation state of the nucleotide so that the resulting modified nucleotide has a base-pairing preference different from the original, unmodified nucleotide. Preferably, the modifying agent modifies unmethylated cytosine. More preferably, the modifying agent is bisulfite salt (e.g., sodium bisulfite). Sodium bisulfite ($NaHSO_3$) reacts with the 5,6-double bond of cytosine, but poorly with methylated cytosine, to form a sulfonated cytosine reaction intermediate. The resulting intermediate is susceptible to deamination, giving rise to a sulfonated uracil. The sulfonate group may then be removed from the sulfonated uracil under alkaline conditions. Methods of treating nucleic acid molecules with sodium bisulfite are well known in the art, see, e.g., Xiong and Laird, *Nucleic Acids Research* 25: 2532–4, 1997; U.S. Pat. Nos. 5,786,146; 6,265,171; 6,331,393; and published PCT applications WO 01/44504 and WO 02/00705.

2. Preparation of Template Nucleic Acids

As described above, after being treated with a modifying agent, a target nucleic acid is used to prepare a fully or partially double-stranded template nucleic acid molecule that comprises a NARS. The template nucleic acid molecule then functions as a template for amplifying a single-stranded nucleic acid fragment in the presence of a NA that recognizes the NARS. The amplified single-stranded nucleic acid fragment is subsequently characterized to determine the methylation state of the target nucleic acid.

The double-stranded template nucleic acid molecule (partially or fully double-stranded) of the present invention may be prepared by the use of an oligonucleotide primer (ODNP) pair, by the use of an adaptor, or by the use of a single ODNP.

a. Using Oligonucleotide Primer Pairs

As noted above, a template double-stranded nucleic acid may be obtained by using an oligonucleotide primer pair. At least one primer of the primer pair comprises a nucleotide sequence of a sense strand of a NARS.

For the embodiments where a target nucleic acid is single-stranded, one ODNP ("first primer" or "forward primer") of the ODNP pair comprises (1) a sequence of a sense strand of a NARS, and (2) a nucleotide sequence at least substantially complementary to a nucleotide sequence ("first nucleotide sequence") of the target nucleic acid. The forward primer is designed so that the first nucleotide sequence to which the forward primer anneals is located 3' to a position (or positions) where a nucleotide (or nucleotides) resides of which the methylation state is of interest and may be determined by the treatment of a particular modifying agent. Such a design allows the extension product of the forward primer to incorporate a nucleotide complementary to the nucleotide that may be differentially modified by the modifying agent. In certain preferred embodiments, the portion(s) of the forward primer other than the sequence of the sense strand of the NARS is completely complementary to its (or their) corresponding sequence(s) in the target nucleic acid. Preferably, there exist sequences located both 5' and 3' to the sequence of the sense strand of the NARS that are complementary to the target. The presence of a complementary sequence located 3' to the sequence of the sense strand of the NARS facilitates annealing of the primer to the template and increases extension/amplification efficiency. The presence of a complementary sequence located 5' to the NARS reduces the number of nucleotides located 3' to the sequence of the sense strand of the NARS that are needed for successful and efficient annealing and extension, and also shortens the length of the subsequently amplified single-stranded nucleic acid molecule as described in detail below. The shortening of the length of the amplified single-stranded nucleic acid molecule facilitates the characterization of this nucleic acid molecule by certain preferred techniques, such as mass spectrometric analysis. The sequence of the sense strand of the NARS of the forward primer may or may not be complementary to the corresponding region of the target. Generally, the forward primer contains at least 6, preferably 8, more preferably 10, most preferably 12, 14 or 16 nucleotides that are complementary to the target nucleic acid.

The other ODNP of the ODNP pair ("second primer" or "reverse primer") comprises a sequence that is at least substantially identical to a second nucleotide sequence of the target nucleic acid. The reverse primer is designed so that the second nucleotide sequence to which the reverse primer anneals is located 5' to a position (or positions) where a nucleotide (or nucleotides) resides of which the methylation state is of interest and may be determined by the treatment of the modifying agent resides. Such a design allows the making and/or amplification of a double-stranded template nucleic acid that comprises both a double-stranded NARS and the nucleotide(s) of which the methylation state is of interest and complementary nucleotides thereof. In certain embodiments, similar to the forward primer, the reverse primer may also comprise a sequence of a sense strand of a NARS. This NARS is preferably the same as the NARS in the forward primer, but may be different from that NARS in the forward primer. The presence of the sequence of the sense strand of a NARS allows shortening the length of an amplified single-stranded nucleic acid fragment ("first amplified single-stranded nucleic acid fragment") using a portion of the template nucleic acid as a template as described below. In addition, it allows the amplification of a single-stranded nucleic acid fragment ("second amplified single-stranded nucleic acid fragment") using the complement of the treated target nucleic acid as a template. The second amplified single-stranded nucleic acid fragment is complementary to the first amplified single-stranded nucleic acid fragment, thus the characterization of the second amplified single-stranded nucleic acid fragment may verify the determination of the methylation state of the target nucleic acid via characterizing the first amplified single-stranded nucleic acid fragment.

At least two extension reactions are needed for making a double-stranded template nucleic acid that comprises a double-stranded NARS and a portion of a target nucleic acid that contains nucleotide(s) of which the methylation state is of interest. The first extension reaction is to extend from the forward primer using the target nucleic acid as a template, while the second is to extend from the reverse primer using the extension product from the forward primer as a template. The resulting double-stranded template nucleic acid or partially double-stranded template nucleic acid may be directly used as a template for amplifying single-stranded nucleic acid fragments. Alternatively, it may go through additional cycle(s) of denaturation, reannealing and extension to produce and/or amplify a double-stranded nucleic acid encompassing the forward and the reverse primers. The double-stranded nucleic acid encompassing the forward and the reverse primers is then used as a template for amplifying single-stranded nucleic acid fragments.

The design of ODNPs where a target nucleic acid is double-stranded is similar to that where a target nucleic acid is single-stranded as described above. More specifically, for the embodiments where a target nucleic acid is double-stranded, one ODNP ("first primer" or "forward primer") comprises (1) a sequence of a sense strand of a NARS, and (2) a nucleotide sequence at least substantially complementary to a nucleotide sequence ("first nucleotide sequence") of the first strand of the target nucleic acid. The other ODNP ("second primer" or "reverse primer") comprises a sequence at least substantially complementary to a second nucleotide sequence of the second strand of the target nucleic acid. The forward and the reverse primers are designed so that the extension/amplification products of the two primers using the target nucleic acid treated with a modifying agent as a template comprise the nucleotide(s) in the target nucleic acid of which the methylation state is of interest. Preferably, the first and second nucleotide sequences of the target nucleic acid are rich in nucleotides that may be differentially modified by the treatment of a modifying agent so that the forward and reverse primers are capable of distinguishing one strand of the treated target nucleic acid from the other, and thus used to perform strand-specific amplification of a portion of the target nucleic acid.

In certain embodiments, the ODNP pair of the present invention may be immobilized to a solid support. In addition, multiple ODNPs may be immobilized to a solid support to form an array of ODNPs. Methods of immobilizing ODNPs are known in the art. Exemplary methods are described in U.S. Pat. Nos. 6,150,103; 5,143,854; 5,424,186; 5,856,101; 5,593,839; 5,908,926; 5,737,257; 6,030,782; 5,760,130; 5,919,626; 6,054,270; 6,040,193; 5,429,807; 5,807,522; 6,110,426; 6,063,339; 6,101,946; and Published PCT Patent Application Nos. WO99/40105; WO99/60156; WO00/35931; WO00/40593, WO99/36760; WO99/05308; WO00/01859; WO00/01798, Stimpson et al. *Proc. Natl. Acad. Sci.* 92:6379–6383 (1995); Beattie et al. *Clin. Chem.* 41:700–706 (1995); Lamture et al. *Nucleic Acids Res.* 22:2121–2125 (1994); Chrisey et al. *Nucleic Acids Res.* 24:3031–3039 (1996); Holmstrom et al., *Anal. Biochem.* 209:278–283 (1993), and PCT application entitled "Methods For Parallel Measurement of Genetic Variations" (PCT/US01/42432).

b. Using Adaptors

As noted above, a template double-stranded nucleic acid may also be obtained by using a nucleic acid adaptor that comprises a NARS. For the embodiments where a target nucleic acid is single-stranded, the adaptor is linked to the target nucleic acid after being treated with a modifying agent and the complement of the treated target nucleic acid so that in the strand that contains a sequence of the antisense strand of a NARS, the treated target nucleic acid is located 5' to the sequence of the antisense strand of the NARS. Such a linkage allows the use of the treated target nucleic acid as a template for amplifying a single-stranded nucleic acid fragment in the presence of the NA that recognizes the NARS and a DNA polymerase, and thus allows the determination of the methylation state of the target nucleic acid. An example of such embodiment is illustrated in FIGS. 5A–H using a NERS as an exemplary NARS. Only the linkage between the adaptor and the treated target nucleic acid shown in FIGS. 5A–D, not in FIGS. 5E–H, may be appropriate to provide a template nucleic acid of the present invention. The linkage between the adaptor and the treated target nucleic acid shown in FIGS. 5A–D is appropriate if the adaptor doest not further comprises a TRERS, or if even the adaptor further comprises a TRERS, the treated target nucleic acid and its complement ligated with the adaptor is not digested by a restriction endonuclease that recognizes the TRERS to provide a template for single-stranded nucleic acid amplification.

Figure 5A:
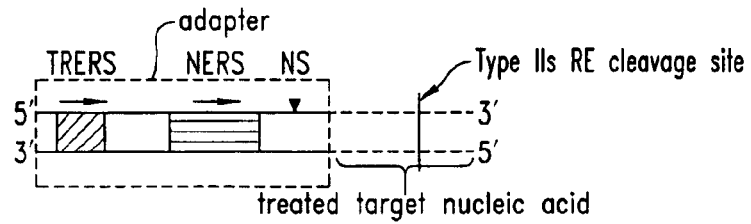
Figure 5B:
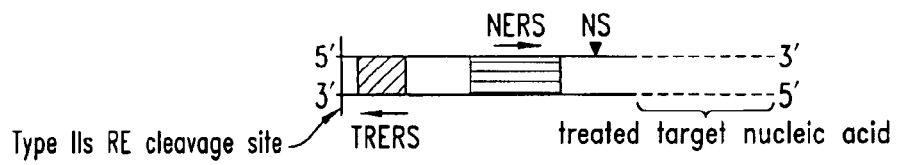
Figure 5C:
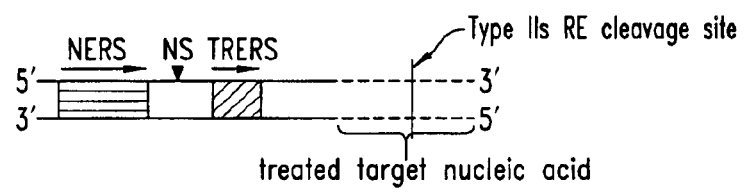
Figure 5D:
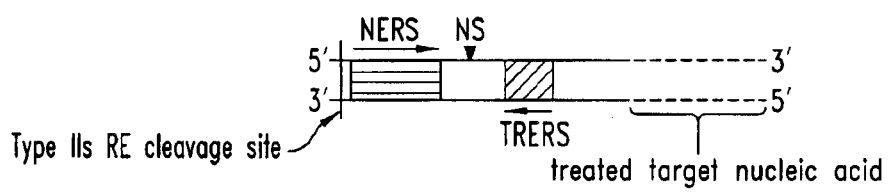

As noted above, in certain embodiments, the nucleic acid adaptor may further comprise a type IIs restriction endonuclease recognition sequence (TRERS). In such embodiments, the TRERS must be located in the adaptor so that when the adaptor is linked to a treated target nucleic acid and the complementary strand thereof in the direction as described above, the cleavage site of a type IIs restriction endonuclease that recognizes the TRERS in the strand that contains a sequence of the antisense strand of the NARS is located both within the treated target nucleic acid and 5' to the position corresponding to the nicking site of a nicking agent that recognizes the NARS. Referring to FIGS. 5A–D, only the arrangement of TRERS and NERS in the adaptor shown in FIGS. 5A and 5C, not in FIGS. 5B and 5D, is appropriate to provide a template nucleic acid of the present invention. Such a location of the TRERS in the adaptor allows the use of a portion of the treated target nucleic acid as a template for amplifying a single-stranded nucleic acid fragment after the treated target nucleic acid and its complementary strand are ligated with the adaptor and the resulting ligation product digested by a type IIs restriction endonuclease that recognizes the TRERS. The presence of the TRERS enables the making of relatively short single-stranded nucleic acid fragments, which facilitates the characterization of these fragments via certain techniques (e.g., mass spectrometric analysis).

Similarly, for the embodiments where a target nucleic acid is double-stranded, the adaptor is linked to the target nucleic acid after being treated with a modifying agent so that in the strand that contains a sequence of the antisense strand of a NARS, the strand of target nucleic acid of which the methylation state is of interest is located 5' to the sequence of the antisense strand of the NARS. In the embodiments where the nucleic acid adaptor further comprises a TRERS, the TRERS is located in the adaptor so that when the adaptor is linked to a treated double-stranded target nucleic acid in the direction as described above, the cleavage site of a type IIs restriction endonucleoase that recognizes the TRERS in the strand that contains the sequence of the antisense strand of the NARS is located both within the treated target nucleic acid and 5' to the position corresponding to the NS of a NA that recognizes the NARS.

The nucleic acid adaptors of the present invention may be prepared by any methods of making short nucleic acid fragments known in the art. For instance, each annealed strand of the nucleic acid adaptors may be synthesized individually and subsequently annealed with its complementary strand.

Any method for directionally linking a nucleic acid adaptor with another double-stranded nucleic acid fragment known in the art may be used to produce a template nucleic acid for synthesizing single-stranded nucleic acid fragments. For instance, if a treated double-stranded target nucleic acid is immobilized to a solid support, then only one terminus of the target nucleic acid is available to be linked with the nucleic acid adaptor. The directional linkage between the available terminus of the treated target nucleic acid and the appropriate terminus of the nucleic acid adaptor (i.e., the 3' terminus of the stand of the adaptor that contains sequence of the antisense strand of the NARS) may be accomplished by designing the adaptor to have the terminus to be ligated to the target to be a blunt end and the other terminus to have either a 3' or a 5' overhang. The presence of the 3' or 5' overhang in the other terminus prevents that terminus from being ligated with the treated target nucleic acid or a fragment thereof.

In certain embodiments, the target nucleic acid is provided by nucleic acid amplification using a primer. The primer may contain a restriction endonuclease recognition sequence (RERS) that is not modified by the treatment of a modifying agent and produces a protruding end upon digestion with a restriction endonuclease that recognizes the RERS. The protruding end may be ligated to a compatible protruding end that is purposefully designed at the appropriate terminus of the nucleic acid adaptor. These compatible protruding ends allow directional linkage between the target nucleic acid and the nucleic acid adaptor. Alternatively, both the terminus of the target nucleic acid and the terminus of the nucleic acid adaptor that are involved in the ligation between the target and the adaptor are blunt, while the other terminus of the target and the other terminus of the adaptor are protruding, but not compatible with each other. The incompatibility between the two protruding termini prevents the ligation between the target and the adaptor at these termini.

In certain embodiments, the adaptor of the present invention may be immobilized to a solid phase. Multiple adaptors of the present invention may be immobilized to form an array of adaptors. Methods of immobilizing nucleic acids are known in the art, and any suitable method may be used to prepare immobilized adaptors or adaptor arrays.

c. Using Single Oligonucleotide Primer

In certain embodiments, a template nucleic acid may be obtained by using a single ODNP. The ODNP comprises a sequence of the sense strand of a NARS. In addition, it is at least substantially complementary to a portion of a target nucleic acid located 3' to a nucleotide, or a portion, of the target of which methylation state is of interest if the target is single-stranded, or to a portion, of one strand of a target nucleic acid located 3' to a nucleotide, or a portion, of the strand of which methylation state is of interest if the target is double-stranded.

Figure 6:
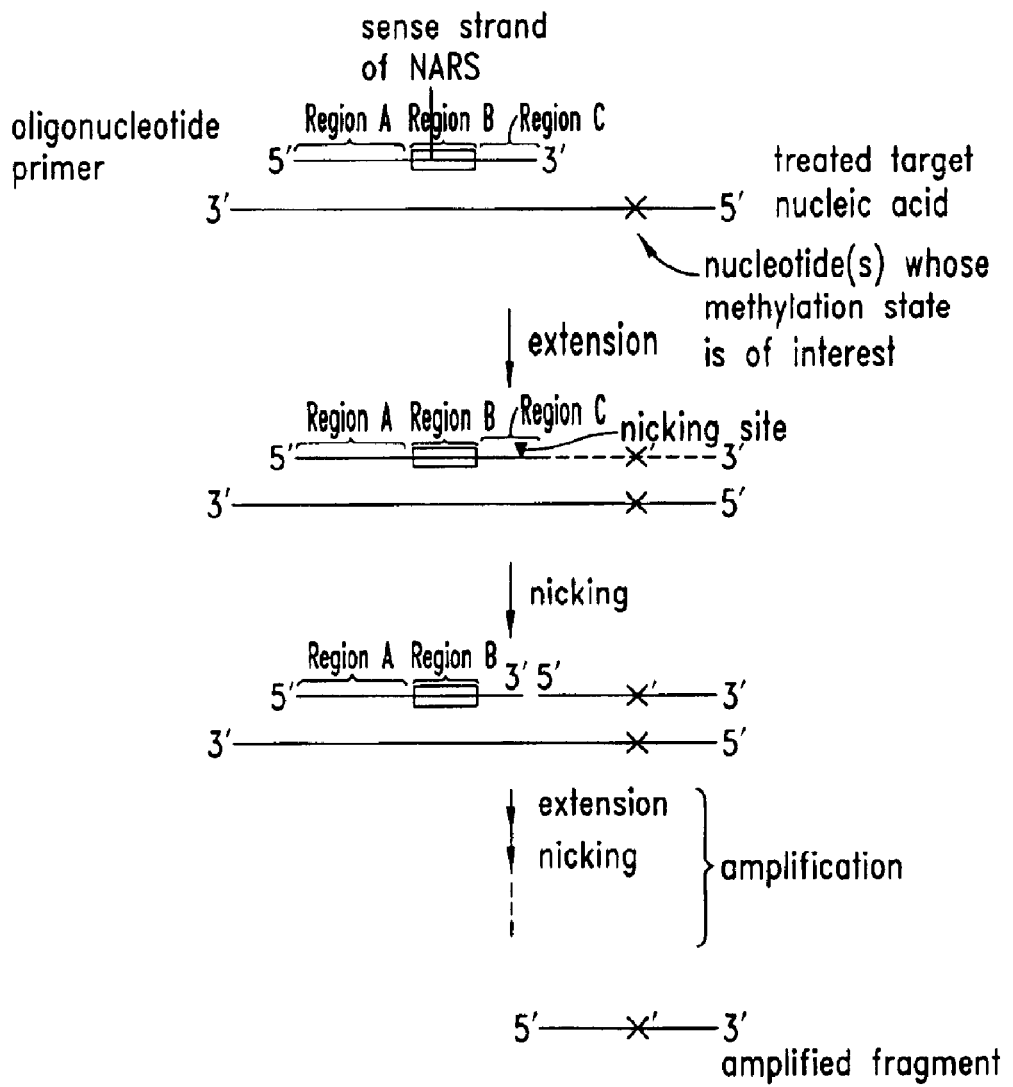
FIG. 6 shows a schematic diagram of a method for amplifying a single-stranded nucleic acid molecule using an oligonucleotide primer that comprises a sequence of the sense strand of a nicking agent recognition sequence. The amplified single-stranded nucleic acid comprises the complement of nucleotide(s) of a target nucleic acid of which methylation state is of interest.

An example of the above embodiments is illustrated in FIG. 6. A single-stranded target nucleic acid is used as an exemplary target nucleic acid, and a NARS recognizable by a nicking agent that nicks outside the NARS is used as an exemplary NA. An oligonucleotide primer is used to amplify a single-stranded nucleic acid molecule using a portion of a single-stranded target nucleic acid that contains the nucleotide(s) (i.e., "X" in FIG. 6) of which methylation state is of interest as a template. The primer comprises, from 5' to 3', three regions: Region A, Region B and Region C. Region B consists of a sequence of the sense strand of a double-stranded nicking agent recognition sequence, where Region A and Region C are regions that are located directly 5' and 3' to Region B, respectively. The oligonucleotide primer is at least substantially complementary to a portion of the target nucleic acid located 3' to the nucleotide(s) X so that under conditions that allow for the amplification of a single-stranded nucleic acid, the oligonucleotide primer is able to anneal to the portion of the target and extends from its 3' terminus in the presence of a DNA polymerase. The resulting extension product (i.e., a template nucleic acid) may be nicked in the presence of a nicking agent that recognizes the double-stranded nicking agent recognition sequence even though there may be one or more nucleotides in Region B of the oligonucleotide primer that do not form conventional base pairs with nucleotides in the target nucleic acid. A "conventional base pair" is a base pair formed according to the standard Watson-Crick model (e.g., G:C, A:T, and A:U) between a nucleotide of one strand of a fully or partially double-stranded nucleic acid and another nucleotide on the other strand of the nucleic acid. The nicked product that contains the 5' terminus may readily dissociate from the target nucleic acid if it is relatively short (e.g., no longer than 18 nucleotides) or be displaced by the extension of the nicked product that contains the 3' terminus at the nicking site. If the nicking agent nicks outside its recognition sequence, the extension product retains Region B of the oligonucleotide primer (i.e., the sequence of the sense strand of the nicking agent recognition sequence) and may thus re-nicked by the nicking agent. The above nicking-extension cycle may be repeated multiple times, resulting in the amplification of a single-stranded nucleic acid molecule that contains the 5' terminus at the nicking site and comprises the complement (i.e., "X'" in FIG. 6) of the nucleotide(s) X.

In certain embodiments, Region B may be a sequence of the sense strand of a NARS that is recognizably by a NA that nicks within its NARS. In such embodiments, the nucleotide(s) in Region B that does not form a conventional base pair with a nucleotide in the target need be located 5' to the nicking site within Region B. After the duplex formed between the oligonucleotide primer and the target or the extension product of the duplex (i.e., a template nucleic acid) is nicked by the nicking agent within Region B, the 3' terminus at the nicking site may be extended to regerate Region B. Such regeneration allows for the repetition of the nicking-extension cycles. In addition, the mismatch(es) between Region B and the corresponding region in the target must not affect the extension from the 3' terminus at the nicking site. Generally, the more distance between the nicking site and the nucleotide(s) in Region B that does not form a conventional base pair, the less adverse effect the mismatch(es) has on the extension.

Region A facilitates or enables the annealing of the oligonucleotide primer to the target nucleic acid. In addition, it facilitates or enables the nicked product that contains the 3' terminus at the nicking site to remain annealing to the target and to extend from the 3' terminus in the presence of a DNA polymerase. In certain embodiments, Region A is at most 100, 75, 50, 25, 20, 15, 14, 13, 12, 11, 10, 9, 8, 7, 6, 5, 4, 3, or 2 nucleotides in length. In some embodiments, there may be one or more nucleotides that do not form conventional base pairs in Region A with the nucleotides in the target nucleic acid.

An oligonucleotide primer may or may not have a Region C. If Region C is present, in certain embodiment, it may be at most 100, 75, 50, 25, 20, 15, 14, 13, 12, 11, 10, 9, 8, 7, 6, 5, 4, 3, 2 or 1 nucleotide(s) in length. There may be mismatch(es) between Region C and its corresponding region in a target nucleic acid. However, the presence of the mismatch(es) need still allow for the nicking of the duplex formed between the oligonucleotide primer and the target or the nicking of the extension product of the duplex. In addition, the presence of the mismatch(es) need still allow for the extension of the nicked product that contains the 3' terminus at the nicking site to extend from that terminus in the presence of a DNA polymerase. If Region C comprises a nicking site nickable by a nicking agent that recognizes Region B, generally, the nucleotides between the 5' terminus of Region C and the nicking site forms conventional base pairs with nucleotides in the target.

In certain embodiments, an oligonucelotide primer of the present invention is immobilized, preferably at its 5' terminus. There may be a linker between the solid phase to which the primer is attached and the 5' or 3' terminus of the primer. In addition, multiple oligonucleotide primers may be immobilized to a single solid phase to produce an array of oligonucleotide primers. The multiple oligonucleotide primers may have identical sequences at discrete locations. Alternatively, they may have different sequences at distinct locations of the array. Such an array may be used to analyze methylation state of multiple target nucleic acid molecules. In certain embodiments, nucleic acid amplification reactions performed at different locations of an array are physically separated, such as in microwells of a plate, so that the amplification products at different locations are not mixed with each other and may be characterized individually.

Figure 7:
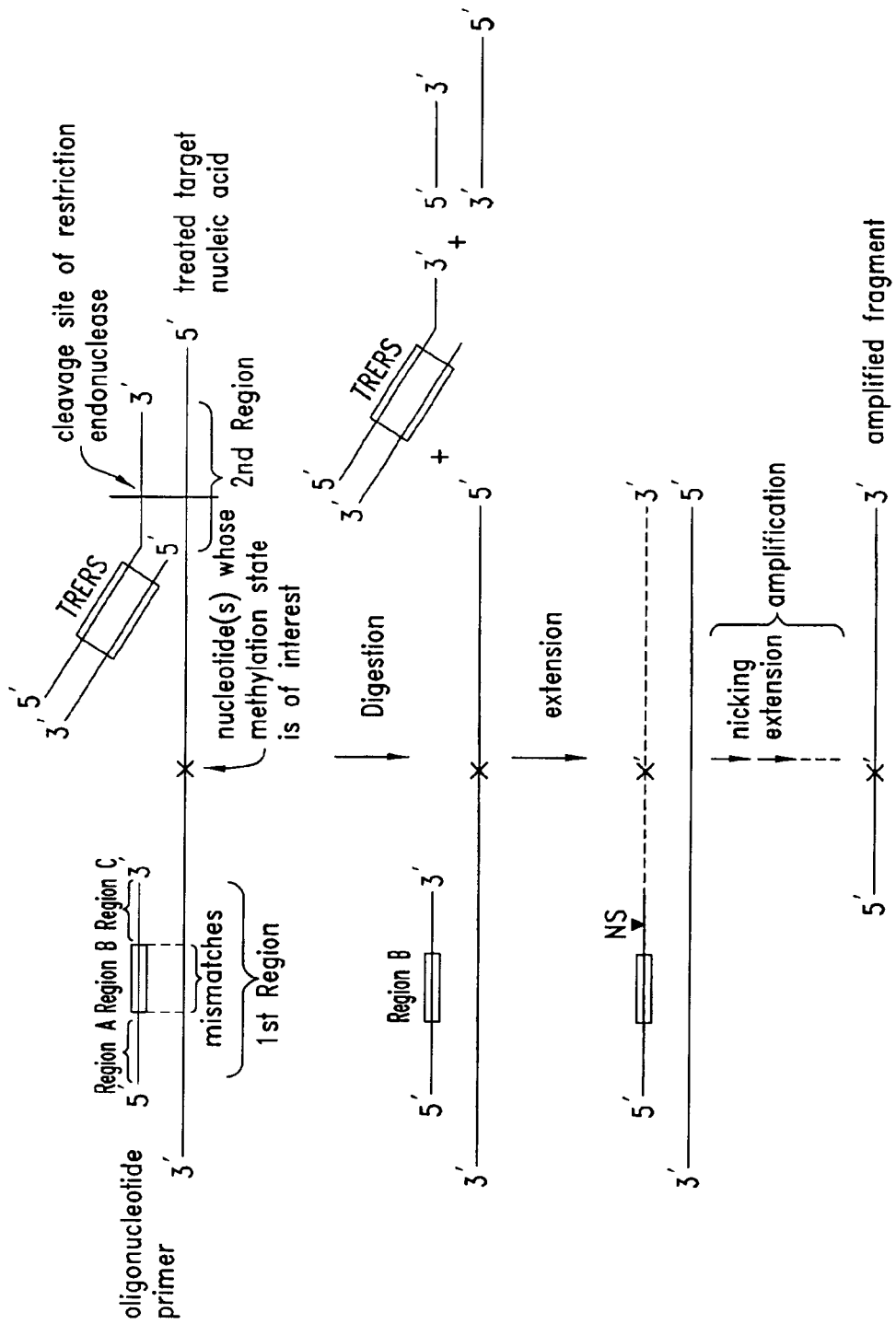
FIG. 7 shows a schematic diagram of a method for amplifying a single-stranded nucleic acid molecule using an oligonucleotide primer that comprises a sequence of the sense strand of a nicking agent recognition sequence and a partially double-stranded nucleic acid molecule that comprise a double-stranded type IIs restriction endonuclease recognition sequence (TRERS). The amplified single-stranded nucleic acid comprises the complement of nucleotide(s) of a target nucleic acid of which methylation state is of interest.

In certain embodiments, it may be desirable to amplify a relatively short single-stranded nucleic acid that comprises the complement of nucleotide(s) of a target nucleic acid of which methylation state is of interest. An example of such embodiments is illustrated in FIG. 7. An oligonucleotide primer that comprises a sequence of the sense strand of a double-stranded nicking agent recognition sequence is annealed to a first region of a single-stranded target nucleic acid located 5' to the nucleotide(s) (i.e., "X" in FIG. 7) of which methylation state is of interest, whereas a partially double-stranded nucleic acid is annealed to a second region of the target nucleic acid located 5' to the nucleotide(s) X. The double-stranded nucleic acid molecule comprises a double-stranded recognition sequence of a type II restriction enzyme recognition sequence (TRERS) in the double-stranded portion and a 3' overhang that is at least substantially, preferably exactly, complementary to a portion of the second region of the target nucleic acid. Because type IIs restriction endonuclease cleaves a nucleic acid outside its double-stranded recognition sequence, the partially double-stranded nucleic acid molecule may be designed to cleave within the duplex formed between the 3' overhang of the partially double-stranded nucleic acid molecule and the second region of the target nucleic acid. Such cleavage results in a shorter fragment of the target nucleic acid to be used as a template to amplify a single-stranded nucleic acid fragment that comprises the complement (i.e., "X'" in FIG. 7) of the nucleotide(s) X.

In certain embodiments, the double-stranded nicking agent recognition sequence of which the sense strand is present in Region B of an oligonucleotide primer may be identical to the double-stranded TRERS. For instance, Region B of the oligonucleotide primer may consist of the sequence "5'-GAGTC-3'" recognizable by a nicking endonuclease N.BstNB I, while the TRERS in the partially double-stranded nucleic acid molecule may be

5'-GAGTC-3'

3'-CTCAG-5' recognizable by type IIs restriction endonuclease PleI and MlyI. In such embodiments, there need be mismatch(es) between Region B of the oligonucleotide primer and the corresponding region in the target nucleic acid. In other words, one or more nucleotides in Region B do not form conventional base pairs with nucleotides in the target. The presence of mismatches prevents the cleavage of the duplex formed between the oligonucleotide primer and the first region of the target by a type IIs restriction endonuclease that recognizes the TRERS.

3. Amplification of Single-Stranded Nucleic Acid Fragments

As described above, the amplification of single-stranded nucleic acid fragments employs cycles of nicking and extension reactions. More specifically, a template nucleic acid that comprises a NARS may be nicked by a NA that recognizes the NARS, producing a 3' terminus and a 5' terminus at the nicking site. The fragment containing the 5' terminus at the nicking site may then readily dissociate from the other portion of the template nucleic acid if it is sufficiently short. Alternatively, it may be displaced and thus dissociate from the other portion of the template nucleic acid by the extension of the 3' terminus at the NS in the presence of a DNA polymerase. The resulting extension product is subsequently re-nicked by the nicking agent, and the recreated 3' terminus at the NS is re-extended. Such a nicking-extension cycles can be repeated multiple times, resulting in the accumulation or amplification of a fragment that contains a 5' terminus at the nicking site.

In certain embodiments, the amplified fragment is relatively short such as a fragment that has at most 200, 150, 100, 75, 50, 40, 30, 25, 20, 18, 16, 14, 12, 10, 9, 8, 7, 6, 5 or 4 nucleotides. The short length of the amplified fragment increases amplification efficiencies and rates, allows for the use of a DNA polymerase that does not have a stand displacement activity, and facilitates the detection of the fragments via certain technologies such as mass spectrometric analysis.

a. Nicking Agents

The nicking agent useful in the present invention may be any agent that fits the definition for a NA as provided above. Preferably, the nicking agent is an enzyme that recognizes a specific sequence of a double-stranded nucleic acid and cleaves only one strand of the nucleic acid. Such an enzyme can be a NE that recognizes a specific sequence that consists of native nucleotides or a RE that recognizes a hemimodified recognition sequence.

A nicking endonuclease may or may not have a nicking site that overlaps with its recognition sequence. An exemplary NE that nicks outside its recognition sequence is N.BstNB I, which recognizes a unique nucleic acid sequence composed of 5'-GAGTC-3', but nicks four nucleotides beyond the 3' terminus of the recognition sequence. The recognition sequence and the nicking site of N.BstNB I are shown below with "▼" to indicate the cleavage site where the letter N denotes any nucleotide:

▼
5'-GAGTCNNNNN-3' (SEQ ID NO:1)

3'-CTCAGNNNNN-5' (SEQ ID NO:2)

N.BstNB I may be prepared and isolated as described in U.S. Pat. No. 6,191,267, incorporated by reference in its entirety. Buffers and conditions for using this nicking endonuclease are also described in the '267 patent. An additional exemplary NE that nicks outside its recognition sequence is N.AlwI, which recognizes the following double-stranded recognition sequence:

▼
5'-GGATCNNNNN-3' (SEQ ID NO:3)

3'-CCTAGNNNNN-5' (SEQ ID NO:4)

The nicking site of N.AlwI is also indicated by the symbol "▼". Both NEs are available from New England Biolabs (NEB). N.AlwI may also be prepared by mutating a type IIs RE AlwI as described in Xu et al. (*Proc. Natl. Acad. Sci. USA* 98:12990–5, 2001).

Exemplary NEs that nick within their NERSs include N.BbvCI-a and N.BbvCI-b. The recognition sequences for the two NEs and the NSs (indicated by the symbol "▼") are shown as follows:

N.BbvCI-a

▼
5'-CCTCAGC-3'

3'-GGAGTCG-5'

N.BbvCI-b

▼
5'-GCTGAGG-3'

3'-CGACTCC-5'

Both NEs are available from NEB.

Additional exemplary nicking endonucleases include, without limitation, N.BstSE I (Abdurashitov et al., *Mol. Biol.* (*Mosk*) 30: 1261–7, 1996), an engineered EcoR V (Stahl et al., *Proc. Natl. Acad. Sci. USA* 93: 6175–80, 1996), an engineered Fok I (Kim et al., *Gene* 203: 43–49, 1997), endonuclease V from *Thermotoga maritima* (Huang et al., *Biochem.* 40: 8738–48, 2001), Cvi Nickases (e.g., CviNY2A, CviNYSI, Megabase Research Porducts, Lincoln, Nebr.) (Zhang et al., *Virology* 240: 366–75, 1998; Nelson et al., *Biol. Chem.* 379: 423–8, 1998; Xia et al., *Nucleic Acids Res.* 16: 9477–87, 1988), and an engineered Mly I (i.e., N.Mly I) (Besnier and Kong, *EMBO Reports* 2: 782–6, 2001). Additional NEs may be obtained by engineering other restriction endonuclease, especially type IIs restriction endonucleases, using methods similar to those for engineering EcoR V, AlwI, Fok I and/or Mly I.

A RE useful as a nicking agent can be any RE that nicks a double-stranded nucleic acid at its hemimodified recognition sequences. Exemplary REs that nick their double-stranded hemimodified recognition sequences include, but are not limited to Ava I, Bsl I, BsmA I, BsoB I, Bsr I, BstN I, BstO I, Fnu4H I, Hinc II, Hind II and Nci I. Additional REs that nick a hemimodified recognition sequence may be screened by the strand protection assays described in U.S. Pat. No. 5,631,147.

Certain nicking agents require only the presence of the sense strand of a double-stranded recognition sequence in an at least partially double-stranded substrate nucleic acid for their nicking activities. For instance, N.BstNB I is active in nicking a substrate nucleic acid that comprises, in one strand, the sequence of the sense strand of its recognition sequence "5'-GAGTC-3'" of which one or more nucleotides do not form conventional base pairs (e.g., G:C, A:T, or A:U) with nucleotides in the other strand of the substrate nucleic acid. The nicking activity of N.BstNB I decreases with the increase of the number of the nucleotides in the sense strand of its recognition sequence that do not form conventional base pairs with any nucleotides in the other strand of the substrate nucleic acid. However, even none of the nucleotides of "5'-GAGTC-3'" form conventional base pairs with the nucleotides in the other strand, N.BstNB I may still retain 10–20% of its optimum activity.

b. DNA Polymerases

The DNA polymerase useful in the present invention may be any DNA polymerase that is 5'→3' exonuclease deficient but has a strand displacement activity. Such DNA polymerases include, but are not limited to, exo⁻ Deep Vent, exo⁻ Bst, exo⁻ Pfu, and exo⁻ Bca. Additional DNA polymerase useful in the present invention may be screened for or created by the methods described in U.S. Pat. No. 5,631,147, incorporated by reference in its entirety. The strand displacement activity may be further enhanced by the presence of a strand displacement facilitator as described below.

Alternatively, in certain embodiments, a DNA polymerase that does not have a strand displacement activity may be used. Such DNA polymerases include, but are not limited to, exo⁻ Vent, Taq, the Klenow fragment of DNA polymerase I, T5 DNA polymerase, and Phi29 DNA polymerase. Typically, the use of these DNA polymerases requires the presence of a strand displacement facilitator. A "strand displacement facilitator" is any compound or composition that facilitates strand displacement during nucleic acid extensions from a 3' terminus at a nicking site catalyzed by a DNA polymerase. Exemplary strand displacement facilitators useful in the present invention include, but are not limited to, BMRF1 polymerase accessory subunit (Tsurumi et al., *J. Virology* 67: 7648–53, 1993), adenovirus DNA-binding protein (Zijderveld and van der Vliet, *J. Virology* 68: 1158–64, 1994), herpes simplex viral protein ICP8 (Boehmer and Lehman, *J. Virology* 67: 711–5, 1993; Skaliter and Lehman, *Proc. Natl. Acad. Sci. USA* 91: 10665–9, 1994), single-stranded DNA binding protein (Rigler and Romano, *J. Biol. Chem.* 270: 8910–9, 1995), phage T4 gene 32 protein (Villemain and Giedroc, *Biochemistry* 35: 14395–4404, 1996), calf thymus helicase (Siegel et al., *J. Biol. Chem.* 267: 13629–35, 1992) and trehalose. In one embodiment, trehalose is present in the amplification reaction mixture.

Additional exemplary DNA polymerases useful in the present invention include, but are not limited to, phage M2 DNA polymerase (Matsumoto et al., *Gene* 84: 247, 1989), phage PhiPRD1 DNA polymerase (Jung et al., *Proc. Natl. Acad. Sci. USA* 84: 8287, 1987), T5 DNA polymerase (Chatterjee et al., *Gene* 97: 13–19, 1991), Sequenase (U.S. Biochemicals), PRD1 DNA polymerase (Zhu and Ito, *Biochim. Biophys. Acta.* 1219: 267–76, 1994), 9°N$_m$™ DNA polymerase (New England Biolabs) (Southworth et al., *Proc. Natl. Acad. Sci.* 93: 5281–5, 1996; Rodriquez et al., *J. Mol. Biol.* 302: 447–62, 2000), and T4 DNA polymerase holoenzyme (Kaboord and Benkovic, *Curr. Biol.* 5: 149–57, 1995).

Alternatively, a DNA polymerase that has a 5'→3' exonuclease activity may be used. For instance, such a DNA polymerase may be useful for amplifying short nucleic acid fragments that automatically dissociate from the template nucleic acid after nicking.

c. Reaction Conditions

According to the methods of the present invention, in a reaction for amplifying a single-stranded nucleic acid fragment, a DNA polymerase may be mixed with a template nucleic acid before, after, or at the same time as, a NA is mixed with the template nucleic acid. Preferably, the nicking-extension reaction buffer is optimized to be suitable for both the NA and the DNA polymerase. For instance, if N.BstNB I is the NA and exo⁻ Vent is the DNA polymerase, the nicking-extension buffer can be 0.5×N.BstNB I buffer and 1×DNA polymerase Buffer. Exemplary 1×N.BstNB I buffer may be 10 mM Tris-HCl, 10 mM MgCl$_2$, 150 mM KCl, and 1 mM dithiothreitol (pH 7.5 at 25° C.). Exemplary 1× DNA polymerase buffer may be 10 mM KCl, 20 mM Tris-HCl (pH 8.8 at 25° C.), 10 mM (NH$_4$)$_2$SO$_4$, 2 mM MgSO$_4$, and 0.1% Triton X-100. One of ordinary skill in the art is readily able to find a reaction buffer for a NA and a DNA polymerase.

In certain preferred embodiments, nicking and extension reactions of the present invention are performed under isothermal conditions. "Isothermally" and "isothermal conditions" refer to a set of reaction conditions where the temperature of the reaction is kept essentially constant (i.e., at the same temperature or within the same narrow temperature range wherein the difference between an upper temperature and a lower temperature is no more than 20° C.) during the course of the amplification. An advantage of the amplification method of the present invention is that there is no need to cycle the temperature between an upper temperature and a lower temperature. Both the nicking and the extension reaction will work at the same temperature or within the same narrow temperature range. If the equipment used to maintain a temperature allows the temperature of the reaction mixture to vary by a few degrees, such a fluctuation is not detrimental to the amplification reaction. Exemplary temperatures for isothermal amplification include, but are not limited to, any temperature between 50° C. to 70° C. or the temperature range between 50° C. to 70° C., 55° C. to 70° C., 60° C. to 70° C., 65° C. to 70° C., 50° C. to 55° C., 50° C. to 60° C., or 50° C. to 65° C. Many NAs and DNA polymerases are active at the above exemplary temperatures or within the above exemplary temperature ranges. For instance, both the nicking reaction using N.BstNB I (New England Biolabs) and the extension reaction using exo⁻ Bst polymerases (BioRad) may be carried out at about 55° C. Other polymerases that are active between about 50° C. and 70° C. include, but are not limited to, exo⁻ Vent (New England Biolabs), exo⁻ Deep Vent (New England Biolabs), exo⁻ Pfu (Strategene), exo⁻ Bca (Panvera), and 9°N$_m$™ DNA polymerase, and Sequencing Grade Taq (Promega).

4. Characterization of Amplified Single-Stranded Nucleic Acid Fragments and Determination of Methylation States of Target Nucleic Acids Any methods known in the art suitable for characterizing a single-stranded nucleic acid may be used in the present invention to obtain the identity (or identities) of a particular nucleotide (or certain nucleotides) in the single-stranded nucleic acid. For instance, a single-stranded nucleic acid amplified using a portion of a target nucleic acid that has been treated with a modifying agent as a template may be directly sequenced. The obtained sequence is then compared with that of a single-stranded nucleic acid amplified using the same portion of a target nucleic acid that has not been treated with a modifying agent. The comparison will indicate whether any of the nucleotides in the portion of the target nucleic acid has been modified and converted to another nucleotide, and thus indicate the methylation state of the portion of the target nucleic acid. In certain embodiments, the nucleotide sequence of a target nucleic acid is known. In those embodiments, the sequence of the single-stranded nucleic acid fragment amplified using a portion of an untreated target nucleic acid may be deduced from the sequence of the known target nucleic acid. The deduced sequence of the single-stranded nucleic acid may, but need not, be determined experimentally.

If the nucleotide of which the methylation state is of interest in a target nucleic acid is within a restriction endonuclease recognition sequence (RERS), the methylation state of this nucleotide may be determined by the use of a restriction endonuclease (RE) that recognizes the RERS. For instance, the amplified single-stranded nucleic acid fragment using a portion of a target nucleic acid that has been treated with a modifying agent as a template may anneal to a nucleic acid fragment that is completely identical to the same portion of the target nucleic acid that has not been treated with a modifying agent. If the nucleotide in the target nucleic acid has not been modified or converted into another nucleotide, the above annealing forms a duplex that contains a RERS. In the presence of a RE that recognizes the RERS, the duplex is digested into two fragments. Thus, the presence of the digestion products indicates that the nucleotide of which the methylation state is of interest has not been modified by the particular modifying agent. Likewise, the absence of any digestion products may indicate that the nucleotide of which the methylation state is of interest has not been modified by the particular modifying agent. The capability or incapability of the modifying agent in converting the nucleotide further indicates the methylation state of the nucleotide.

In certain related embodiments, a restriction endonuclease may also be used to determine the methylation state of a nucleotide in a target nucleic acid where a nucleotide derived or converted from the nucleotide in the target nucleic acid by a modifying agent is within a recognition sequence of the restriction endonuclease. For instance, the amplified single-stranded nucleic acid fragment using a portion of a target nucleic acid that has been treated with a modifying agent as a template may anneal to another single-stranded nucleic acid fragment. The other single-strand nucleic acid fragment is completely identical to the same portion of the target nucleic acid that has been treated with a modifying agent with the assumption that the nucleotide of which the methylation state is of interest in the target nucleic acid is converted to another nucleotide by the modifying agent. If the nucleotide in the target nucleic acid has indeed been modified or converted into another nucleotide, the above annealing forms a duplex that contains the RERS. In the presence of a RE that recognizes the RERS, the duplex is digested into two fragments. Thus, the presence of the digestion products indicates that the nucleotide of which the methylation state is of interest has been modified by the particular modifying agent. Likewise, the absence of any digestion products indicates that the nucleotide of which the methylation state is of interest has not been modified by the particular modifying agent. The ability or inability of the modifying agent in modifying the nucleotide of interest further indicates the methylation state of the nucleotide.

In certain embodiments, single nucleotide primer extension may be used to characterize an amplified single-stranded nucleic acid fragment. For instance, the amplified single-stranded nucleic acid fragment may anneal to a primer having a sequence identical to a portion of a target nucleic acid directly 3' to the nucleotide of which the methylation state is of interest. In the presence of a labeled nucleotide that is capable of base pairing with the nucleotide of which the methylation state is of interest, the incorporation of the labeled nucleotide via the extension of the above primer will indicate that the particular nucleotide in the target nucleic acid has not been modified by the treatment of a modifying agent. On the other hand, the inability to incorporate the labeled nucleotide may indicate that the particular nucleotide in the target nucleic acid has been modified by the treatment of a modifying agent so that the resulting modified nucleotide is no longer complementary to the labeled nucleotide. A similar process where sodium bisulfite is used as a modifying agent is described in Gonzalgo and Jones, *Nucleic Acids Res.* 25: 2529–31, 1997.

Another technique that is useful in characterizing an amplified single-stranded nucleic acid fragment is mass spectrometry. Before subjecting the amplified single-stranded nucleic acid fragment to mass spectrometric analysis, the above nucleic acid fragment may, or may not, be at least partially purified by techniques such as liquid chromatography and electrophoresis. The molecular weight of an amplified single-stranded fragment determined by mass spectrometric analysis may be compared with the predicted molecular weights of two single-stranded fragments, respectively: one fragment amplified using a portion of a target nucleic acid where the nucleotide of which methylation state is of interest is assumed to remain the same after the treatment of a modifying agent, the other amplified using the portion of the target nucleic acid where the nucleotide of which methylation state is of interest is assumed to be converted to another nucleotide by the treatment of the modifying agent. The above comparison may indicate whether the nucleotide of which the methylation state is of interest has, or has not, been modified by the modifying agent. Based on the above indication, one may determine the methylation state of the nucleotide of interest in the target nucleic acid. Detailed descriptions of mass spectrometric analysis as well as other techniques useful in characterizing single-stranded nucleic acid fragment may be found in U.S. Prov. Appl. Nos. 60/305,637 and 60/345,445.

Many of the techniques for characterizing amplified single-stranded nucleic acid fragments may also be used to measure the amount of a particular amplified single-stranded nucleic acid fragment in an amplification reaction mixture. For instance, in the embodiments where an amplified single-stranded nucleic acid molecule is first separated from the other molecules in the amplification reaction mixture by liquid chromatography and then subject to mass spectrometric analysis, the amount of the amplified single-stranded nucleic acid molecule may be quantified either by liquid chromatography of the fraction that contains the nucleic acid molecule, or by ion current measurement of the mass spectrometric peak corresponding to the nucleic acid molecule. Such techniques may be used to determine the percentage of a target nucleic acid molecule that has a methylated nucleotide at a defined position in a nucleic acid population that also contains the target nucleic acid molecule that has an unmethylated nucleotide at the defined position.

Many of the techniques for characterizing amplified single-stranded nucleic acid fragments may also be used in multiplex determination of methylation states of multiple target nucleic acids in a nucleic acid population. For instance, mass spectrometry allows characterizations of multiple single-stranded nucleic acid fragments in a high throughput format. Each of the multiple single-stranded nucleic acid fragments may be amplified using a primer pair specific to a particular target nucleic acid as primers and a portion of the particular target nucleic acid treated by a modifying agent as a template. Characterization of the amplified single-stranded nucleic acid fragments enables the determination of the methylation state of target nucleic acids.

C. Compositions and Kits Useful in Methylation Analysis

In one aspect, the present invention also provides compositions and kits for nucleic acid methylation analysis. In certain embodiments, the composition or kit of the present invention comprises a double-stranded template nucleic acid that comprises a NARS and a target nucleic acid that has been treated by a modifying agent. This double-stranded template nucleic acid may be prepared by the use of a nucleic acid adaptor that comprises a NARS as described above. In some other embodiments, the composition or kit of the present invention comprises a target nucleic acid that has been treated with a modifying agent and a primer pair used in obtaining a double-stranded template nucleic acid as described above.

The composition or kit of the present invention may further comprise one, two, or more of the following components: (1) a nicking agent that recognizes the NARS in the double-stranded template nucleic acid (e.g., N.BstNB I) and/or a buffer thereof; (2) a DNA polymerase (e.g., 9°N$_m$™ DNA polymerase) and/or a buffer thereof; (3) a strand displacement facilitator (e.g., trehalose); (4) one or more deoxynucleoside triphosphate(s); (4) a chromatography column; (5) a buffer for phase A (Buffer A) of the chromatography; and (6) a buffer for phase B (Buffer B) of the chromatography. The kit of the present invention may further comprise an instruction booklet for using the kit. Detailed description of the above components may be found in U.S. Prov. Appl. No. 60/345,445.

The following example is provided by way of illustration and not limitation.

EXAMPLE

Nucleic Acid Amplification Using Template Nucleic Acid Comprising Mismatches in Nickign Agent Recognition Sequence The following oligonucleotides were synthesized and obtained from MWG (MWG Biotech Inc., High Point, N.C.). The oligonucleotides were placed in 0.01 M Tris-HCl and 0.001 M EDTA at 100 pmoles per microliter. The sequence of the sense strand of the double-stranded recognition sequence of N.BstNB I is underlined whereas the nucleotide(s) that is different from the nucleotide at the corresponding position(s) of the antisense strand of the double-stranded recognition sequence of N.BstNB I is italicized

```
B-1:   5' CC TAC GAC TGG AAC AGA CTC ACC TAC GAC TGG A- 3'
       (SEQ ID NO: 5)

B-2:   5' CC TAC GAC TGG AAC AAT AAA ACC TAC GAC TGG A- 3'
       (SEQ ID NO: 6)

B-3:   5' CC TAC GAC TGG AAC AGA TTC ACC TAC GAC TGG A- 3'
       (SEQ ID NO: 7)

B-4:   5' CC TAC GAC TGG AAC AGA CAC ACC TAC GAC TGG A- 3'
       (SEQ ID NO: 8)

B-5:   5' CC TAC GAC TGG AAC AGT CTC ACC TAC GAC TGG A- 3'
       (SEQ ID NO: 9)

B-6:   5' CC TAC GAC TGG AAC AGA AAC ACC TAC GAC TGG A- 3'
       (SEQ ID NO: 10)

B-7:   5' CC TAC GAC TGG AAC AGT AAC ACC TAC GAC TGG A- 3'
       (SEQ ID NO: 11)

T-1:   3' GG ATG CTG ACC TTG TCT GAG TGG ATG CTG ACC T- 5'
       (SEQ ID NO: 12)

T-1a:  3' GG ATG CTG ACC TTG TCT GAG TGG ATG CTG ACC T- 5'
       (SEQ ID NO: 12)

T-1b:  3' GG ATG CTG ACC TTG TCT GAG TGG ATG CTG ACC - 5'
       (SEQ ID NO: 13)

T-1c:  3' GG ATG CTG ACC TTG TCT GAG TGG ATG CTG AC- 5'
       (SEQ ID NO: 14)

T-1d:  3' GG ATG CTG ACC TTG TCT GAG TGG ATG CTG A- 5'
       (SEQ ID NO: 15)

T-1e:  3' GG ATG CTG ACC TTG TCT GAG TGG ATG CTG - 5'
       (SEQ ID NO: 16)

T-1f:  3' GG ATG CTG ACC TTG TCT GAG TGG ATG CT- 5'
       (SEQ ID NO: 17)

T-1g:  3' GG ATG CTG ACC TTG TCT GAG TGG ATG C- 5'
       (SEQ ID NO: 18)

T-1h:  3' GG ATG CTG ACC TTG TCT GAG TGG ATG- 5'
       (SEQ ID NO: 19)

T-1i:  3' GG ATG CTG ACC TTG TCT GAG TGG AT- 5'
       (SEQ ID NO: 20)

T-1j:  3' GG ATG CTG ACC TTG TCT GAG TGG A- 5'
       (SEQ ID NO: 21)
```

```
T-1k:  3' GG ATG CTG ACC TTG TCT GAG TGG - 5'
       (SEQ ID NO: 22)

T-1l:  3' GG ATG CTG ACC TTG TCT GAG TG- 5'
       (SEQ ID NO: 23)

T-1m:  3' GG ATG CTG ACC TTG TCT GAG T- 5'
       (SEQ ID NO: 24)

T-1n:  3' GG ATG CTG ACC TTG TCT GAG - 5'
       (SEQ ID NO: 25)
```

The following mixture was combined and then 25 microliters of the mixture was added to each well in the microtiter plate.

- 250 ul 10×Thermopol buffer (NEB Biolabs, Beverly, Mass.)
- 125 ul 10×N.BstNBI (NEB Biolabs, Beverly, Mass.)
- 100 ul 25 mM dNTPs (NEB Biolabs, Beverly, Mass.)
- 1000 ul 1 M trehalose (Sigma, St. Louis, Mo.)
- 250 units N.BstNBI nicking enzyme (NEB Biolabs, Beverly, Mass.)
- 50 units Vent exo- DNA polymerase (NEB Biolabs, Beverly, Mass.)
- 1020 ul ultra pure water 25 microliters of each respective duplex was then added to the microtiter plate. The duplex was formed by first diluting two oligonucleotide primers and placing them in the following solution at a final concentration of 1 pmole per microliter: 1×Thermopol buffer (New England Biolabs, Beverly, Mass.) and 0.5×N.BstNBI buffer. The 1×Thermopol buffer consists of 10 mM KCl, 10 mM $(NH_4)_2SO_4$, 20 mM Tris-HCl pH8.8, 0.1% Triton X-100, 2 mM $MgSO_4$, whereas the 1×N.BstNBI buffer consists of 150 mM KCl, 10 mM Tris-HCl, 10 mM $MgCl_2$, 1 mM DTT. The mixture was then heated to 100° C. for 1 minute and then held at 50° C. for 10 minutes to allow the duplexes to form. The plate was resealed at 4° C., and then heated to 60° C. for 1 hour.

The following duplexes were tested:

1 (perfect base pairing) [T-1 and B-1 SEQ ID NOS: 12 and 5 respectively]

```
T-1: 3' GG ATG CTG ACC TTG TCT GAG TGG ATG CTG ACC T- 5'
B-1: 5' CC TAC GAC TGG AAC AGA CTC ACC TAC GAC TGG A- 3'
```

2 (complete mismatching) [T-1 and B-2 SEQ ID NOS: 12 and 6 respectively]

```
T-1: 3' GG ATG CTG ACC TTG TCT GAG TGG ATG CTG ACC T- 5'
B-2: 5' CC TAC GAC TGG AAC AAT AAA ACC TAC GAC TGG A- 3'
```

3 (single mismatch) [T-1 and B-3 SEQ ID NOS: 12 and 7 respectively]

```
T-1: 3' GG ATG CTG ACC TTG TCT GAG TGG ATG CTG ACC T- 5'
B-3: 5' CC TAC GAC TGG AAC AGA TTC ACC TAC GAC TGG A- 3'
```

4 (single mismatch) [T-1 and B-4 SEQ ID NOS: 12 and 8 respectively]

```
T-1: 3' GG ATG CTG ACC TTG TCT GAG TGG ATG CTG ACC T- 5'
B-4: 5' CC TAC GAC TGG AAC AGA CAC ACC TAC GAC TGG A- 3'
```

5 (single mismatch) [T-1 and B-5 SEQ ID NOS: 12 and 9 respectively]

```
T-1: 3' GG ATG CTG ACC TTG TCT GAG TGG ATG CTG ACC T- 5'
B-5: 5' CC TAC GAC TGG AAC AGT CTC ACC TAC GAC TGG A- 3'
```

6 (2 mismatches) [T-1 and B-6 SEQ ID NOS: 12 and 10 respectively]

```
T-1: 3' GG ATG CTG ACC TTG TCT GAG TGG ATG CTG ACC T- 5'
B-6: 5' CC TAC GAC TGG AAC AGA AAC ACC TAC GAC TGG A- 3'
```

7 (3 mismatches) [T-1 and B-7 SEQ ID NOS: 12 and 11 respectively]

```
T-1: 3' GG ATG CTG ACC TTG TCT GAG TGG ATG CTG ACC T- 5'
B-7: 5' CC TAC GAC TGG AAC AGT AAC ACC TAC GAC TGG A- 3'
```

8a. (T-1 and B-7 SEQ ID NOS: 12 and 11 respectively)

```
T-1: 3' GG ATG CTG ACC TTG TCT GAG TGG ATG CTG ACC T- 5'
B-7: 5' CC TAC GAC TGG AAC AGT AAC ACC TAC GAC TGG A- 3'
```

8b. (T-1 and B-7 SEQ ID NOS: 13 and 11 respectively)

```
T-1: 3' GG ATG CTG ACC TTG TCT GAG TGG ATG CTG ACC - 5'
B-7: 5' CC TAC GAC TGG AAG AGT AAC ACC TAC GAC TGG A- 3'
```

8c. (T-1 and B-7 SEQ ID NOS: 14 and 11 respectively)

```
T-1: 3' GG ATG CTG ACC TTG TCT GAG TGG ATG CTG AC- 5'
B-7: 5' CC TAC GAC TGG AAC AGT AAC ACC TAC GAC TGG A- 3'
```

8d. (T-1 and B-7 SEQ ID NOS: 15 and 11 respectively)

```
T-1: 3' GG ATG CTG ACC TTG TCT GAG TGG ATG CTG A- 5'
B-7: 5' CC TAC GAC TGG AAC AGT AAC ACC TAC GAC TGG A- 3'
```

8e. (T-1 and B-7 SEQ ID NOS: 16 and 11 respectively)

```
T-1: 3' GG ATG CTG ACC TTG TCT GAG TGG ATG CTG - 5'
B-7: 5' CC TAC GAC TGG AAC AGT AAC ACC TAC GAC TGG A- 3'
```

8f. (T-1 and B-7 SEQ ID NOS: 17 and 11 respectively)

```
T-1: 3' GG ATG CTG ACC TTG TCT GAG TGG ATG CT- 5'
B-7: 5' CC TAC GAC TGG AAC AGT AAC ACC TAC GAC TGG A- 3'
```

8g. (T-1 and B-7 SEQ ID NOS: 18 and 11 respectively)

```
T-1: 3' GG ATG CTG ACC TTG TCT GAG TGG ATG C- 5'
B-7: 5' CC TAC GAC TGG AAC AGT AAC ACC TAC GAC TGG A- 3'
```

8h. (T-1 and B-7 SEQ ID NOS: 19 and 11 respectively)

```
T-1: 3' GG ATG CTG ACC TTG TCT GAG TGG ATG - 5'
B-7: 5' CC TAC GAC TGG AAC AGT AAC ACC TAC GAC TGG A- 3'
```

8i. (T-1 and B-7 SEQ ID NOS: 20 and 11 respectively)

```
T-1: 3' GG ATG CTG ACC TTG TCT GAG TGG AT- 5'
B-7: 5' CC TAC GAC TGG AAC AGT AAC ACC TAC GAC TGG A- 3'
```

8j. (T-1 and B-7 SEQ ID NOS: 21 and 11 respectively)

```
T-1: 3' GG ATG CTG ACC TTG TCT GAG TGG A- 5'
B-7: 5' CC TAC GAC TGG AAC AGT AAC ACC TAC GAC TGG A- 3'
```

8k. (T-1 and B-7 SEQ ID NOS: 22 and 11 respectively)

```
T-1: 3' GG ATG CTG ACC TTG TCT GAG TGG - 5'
B-7: 5' CC TAC GAC TGG AAC AGT AAC ACC TAC GAC TGG A- 3'
```

8l. (T-1 and B-7 SEQ ID NOS: 23 and 11 respectively)

```
T-1: 3' GG ATG CTG ACC TTG TCT GAG TG- 5'
B-7: 5' CC TAC GAC TGG AAC AGT AAC ACC TAC GAC TGG A- 3'
```

8m. (T-1 and B-7 SEQ ID NOS: 24 and 11 respectively)

```
T-1: 3' GG ATG CTG ACC TTG TCT GAG T- 5'
B-7: 5' CC TAC GAC TGG AAC AGT AAC ACC TAC GAC TGG A- 3'
```

8n. (T-1 and B-7 SEQ ID NOS: 25 and 11 respectively)

```
T-1: 3' GG ATG CTG ACC TTG TCT GAG - 5'
B-7: 5' CC TAC GAC TGG AAC AGT AAC ACC TAC GAC TGG A- 3'
```

9a. (T-1 and B-2 SEQ ID NOS: 12 and 6 respectively)

```
T-1: 3' GG ATG CTG ACC TTG TCT GAG TGG ATG CTG ACC T- 5'
B-2: 5' CC TAC GAC TGG AAC AAT AAA ACC TAC GAC TGG A- 3'
```

9b. (T-1 and B-2 SEQ ID NOS: 13 and 6 respectively)

```
T-1: 3' GG ATG CTG ACC TTG TCT GAG TGG ATG CTG ACC - 5'
B-2: 5' CC TAC GAC TGG AAC AAT AAA ACC TAC GAC TGG A- 3'
```

9c. (T-1 and B-2 SEQ ID NOS: 14 and 6 respectively)

```
T-1: 3' GG ATG CTG ACC TTG TCT GAG TGG ATG CTG AC- 5'
B-2: 5' CC TAC GAC TGG AAC AAT AAA ACC TAC GAC TGG A- 3'
```

9d. (T-1 and B-2 SEQ ID NOS: 15 and 6 respectively)

```
T-1: 3' GG ATG CTG ACC TTG TCT GAG TGG ATG CTG A- 5'
B-2: 5' CC TAC GAC TGG AAC AAT AAA ACC TAC GAC TGG A- 3'
```

9e. (T-1 and B-2 SEQ ID NOS: 16 and 6 respectively)

```
T-1: 3' GG ATG CTG ACC TTG TCT GAG TGG ATG CTG - 5'
B-2: 5' CC TAC GAC TGG AAC AAT AAA ACC TAC GAC TGG A- 3'
```

9f. (T-1 and B-2 SEQ ID NOS: 17 and 6 respectively)

```
T-1: 3' GG ATG CTG ACC TTG TCT GAG TGG ATG CT- 5'
B-2: 5' CC TAC GAC TGG AAC AAT AAA ACC TAC GAC TGG A- 3'
```

9g. (T-1 and B-2 SEQ ID NOS: 18 and 6 respectively)

```
T-1: 3' GG ATG CTG ACC TTG TCT GAG TGG ATG C- 5'
B-2: 5' CC TAC GAC TGG AAC AAT AAA ACC TAC GAC TGG A- 3'
```

9h. (T-1 and B-2 SEQ ID NOS: 19 and 6 respectively)

```
T-1: 3' GG ATG CTG ACC TTG TCT GAG TGG ATG - 5'
B-2: 5' CC TAC GAC TGG AAC AAT AAA ACC TAC GAC TGG A- 3'
```

9i. (T-1 and B-2 SEQ ID NOS: 20 and 6 respectively)

```
T-1: 3' GG ATG CTG ACC TTG TCT GAG TGG AT- 5'
B-2: 5' CC TAC GAC TGG AAC AAT AAA ACC TAC GAC TGG A- 3'
```

9j. (T-1 and B-2 SEQ ID NOS: 21 and 6 respectively)

```
T-1: 3' GG ATG CTG ACC TTG TCT GAG TGG A- 5'

B-2: 5' CC TAC GAC TGG AAC AAT AAA ACC TAC GAC TGG A- 3'
```

9k. (T-1 and B-2 SEQ ID NOS: 22 and 6 respectively)

```
T-1:  3' GG ATG CTG ACC TTG TCT GAG TGG ATG CT- 5'

B-2:  5' CC TAC GAC TGG AAC AAT AAA ACC TAG GAG TGG A- 3'
```

9l. (T-1 and B-2 SEQ ID NOS: 23 and 6 respectively)

```
T-1:  3' GG ATG CTG ACC TTG TCT GAG TGG ATG C- 5'

B-2:  5' CC TAC GAC TGG AAC AAT AAA ACC TAC GAC TGG A- 3'
```

9m. (T-1 and B-2 SEQ ID NOS: 24 and 6 respectively)

```
T-1:  3' GG ATG CTG ACC TTG TCT GAG T- 5'

B-2:  5' CC TAC GAC TGG AAC AAT AAA ACC TAC GAC TGG A- 3'
```

9n. (T-1 and B-2 SEQ ID NOS: 25 and 6 respectively)

```
T-1:  3' GG ATG CTG AGG TTG TCT GAG - 5'

B-2:  5' CC TAG GAC TGG AAC AAT AAA ACC TAC GAC TGG A- 3'
```

The plate was loaded onto the LC/MS (Micromass LTD, Manchester UK and Beverly, Mass., USA) that is a LCT time-of-flight uisng electrospray in the negative mode. The conditions were as follows:

The chromatography system was an Agilent HPLC-1100 composed of a binary pump, degasser, a column oven, a diode array detector, and thermostatted microwell plate autoinjector (Palo Alto, Calif.). The column was a Waters Xterra, incorporating C18 packing with 3 uM particle size, with 300 Angstrom pore size, 2.1 mm×50 mm (Waters Inc. Milford, Mass.). The column was run at 30 C with a gradient of acetonitrile in 5 mM Triethylamine acetate (TEAA). Buffer A was 5 mM TEAA, buffer B was 5 mM TEAA and 25% (VN) acetonitrile. The gradient began with a hold at 10% B for one minute then ramped to 50% B over 4 minutes followed by 30 seconds at 95% B and finally returned to 10% B for a total run time of six minutes. The column temperature was held constant at 30 C. The flow rate was 0.416 ml per minute. The injection volume was 10 microliters. Flow into the mass spectrometer was 200 ul/min, half the LC flow was diverted to waste using a tee. The mass spectrometer wass a Micromass LCT Time-of-Flight with an electrospray inlet (Micromass Inc. Manchester UK). The samples were run in electrospary negative mode with a scan range from 700 to 2300 amu using a 1 second scan time.

Instrument parameters were: TDC start voltage 700, TDC stop voltage 50, TDC threshold 0, TDC gain control 0, TDC edge control 0, Lteff 1117.5, Veff 4600. Source parameters: Desolvation gas 862 L/hr, Capillary 3000V, Sample cone 25V, RF lens 200V, extraction cone 2V, desolvation temperature 250 C, Source temperature 150 C, RF DC offset 14V, FR DC offset 21V, Aperture 6V, accelaration 200V, Focus, 10V, Steering 0V, MCP detector 2700V, Pusher cycle time (manual) 60, Ion energy 40V, Tube lens 0V, Grid 274V, TOF flight tube 4620V, Reflectron 1790V.

The following extracted ion currents were monitored: 1144.7 daltons plus or minus 1 dalton around 1144.7 for the following fragment to be released:

```
3' GG ATG CTG ACC-5'
(SEQ ID NO: 26)
``` from the following duplex, as well as the other duplexes listed above:

(T-1 and B-1 SEQ ID NOS: 12 and 5 respectively)
T-1:   3' GG ATG CTG ACC TTG TCT GAG TGG ATG CTG ACC T- 5'

B-1:   5' CC TAC GAC TGG AAC AGA CTC ACC TAC GAC TGG A- 3'

The results are shown in the table below:

| Duplex Names | Number of Mismatches Within Double-Stranded N.BstNB1 Recognition Sequence | Relative Mass Units Observed |
|---|---|---|
| 1 | 0 | 121.0 |
| 2 | 5 | 18.5 |
| 3 | 1 | 66.7 |
| 4 | 1 | 61.5 |
| 5 | 1 | 63.0 |
| 6 | 2 | 45.0 |
| 7 | 3 | 21.2 |
| 8a | 3 | 23.4 |
| 8b | 3 | 28.3 |
| 8c | 3 | 11.5 |
| 8d | 3 | 29.2 |
| 8e | 3 | 14.6 |
| 8f | 3 | 17.8 |
| 8g | 3 | 20.8 |
| 8h | 3 | 12.3 |
| 8i | 3 | 14.9 |
| 8j | 3 | 18.3 |
| 8k | 3 | 19.3 |
| 8l | 3 | 15.6 |
| 8m | 3 | 18.3 |
| 8n | 3 | 12.5 |
| 9a | 5 | 21.3 |
| 9b | 5 | 17.8 |
| 9c | 5 | 19.2 |
| 9d | 5 | 15.3 |
| 9e | 5 | 14.0 |
| 9f | 5 | 15.9 |
| 9g | 5 | 28.3 |
| 9h | 5 | 22.7 |
| 9i | 5 | 23.9 |
| 9j | 5 | 21.4 |
| 9k | 5 | 22.6 |
| 9l | 5 | 22.5 |
| 9m | 5 | 13.5 |
| 9n | 5 | 14.3 |

All of the above U.S. patents, U.S. patent application publications, U.S. patent applications, foreign patents, foreign patent applications and non-patent publications referred to in this specifications and/or listed in the Application Data Sheet, are incorporated by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for characterizing the methylation state of a target nucleic acid, comprising:
   a. treating the target nucleic acid with a modifying agent that differentially modifies a nucleotide based on the methylation state of the nucleotide to provide a treated target nucleic acid;
   b. providing a template double-stranded nucleic acid that comprises a nicking agent recognition sequence (NARS) and a portion of the treated target nucleic acid or an amplification product thereof if the target nucleic acid is single-stranded or a portion of one strand of the treated target nucleic acid if the target nucleic acid is double-stranded;
   c. amplifying a single-stranded nucleic acid fragment in the presence of a nicking agent (NA) that recognizes the NARS, a DNA polymerase, and one or more deoxynucleoside triphosphate(s), wherein the amplifying uses a portion of the template double-stranded nucleic acid as a template, wherein the single-stranded nucleic acid fragment contains no more than 20 nucleotides; and
   d. characterizing the single-stranded nucleic acid fragment and thereby characterizing the methylation state of the target nucleic acid.

2. The method of claim 1 wherein the modifying agent is a bisulfite salt.

3. The method of claim 2 wherein the modifying agent is sodium bisulfite.

4. The method of claim 1 wherein the NA is a nicking endonuclease (NE).

5. The method of claim 4 wherein the NE is N.BstNB I.

6. The method of claim 1 wherein the target nucleic acid is single-stranded.

7. The method of claim 6 wherein the target nucleic acid is one strand of a denatured double-stranded nucleic acid.

8. The method of claim 1 wherein the DNA polymerase is selected from the group consisting of exo⁻ Vent DNA polymerase, exo⁻ Deep Vent DNA polymerase, exo⁻ Bst DNA polymerase, 9°N$_m$™ DNA polymerase and exo⁻ Bca DNA polymerase.

9. The method of claim 1 wherein the characterizing is performed at least partially by the technique selected from the group consisting of spectrometry, chromatography, and electrophoresis.

10. The method of claim 1 wherein the providing is performed by the steps, comprising
   (1) forming a mixture comprising the treated target nucleic acid, a first oligonucleotide primer (ODNP) and a second ODNP, wherein
      (a) if the target nucleic acid is single-stranded,
         the first ODNP comprises a sequence of a sense strand of a NARS, and a nucleotide sequence at least substantially complementary to a first nucleotide sequence of the target nucleic acid,
         the second ODNP comprises a sequence at least substantially identical to a second nucleotide sequence of the target nucleic acid, the second nucleotide sequence located 5' to the first nucleotide sequence; or
      (b) if the target nucleic acid is double-stranded having a first strand and a second strand,
         the first ODNP comprises a sequence of a sense strand of a NARS and a nucleotide sequence at least substantially complementary to a first nucleotide sequence of the first strand of the target nucleic acid,
         the second ODNP comprises a sequence at least substantially complementary to a second nucleotide sequence of the second strand of the target nucleic acid, the nucleotide sequence in the first strand of the target nucleic acid that corresponds to the second nucleotide sequence in the second strand of the target nucleic acid being located at 5' to the first nucleotide sequence in the first strand of the target nucleic acid; and
   (2) maintaining said mixture at conditions that amplify a template double-stranded nucleic acid that comprises the NARS.

11. The method of claim 1 wherein the providing is performed by the steps, comprising
   (a) if the target nucleic acid is single-stranded,
      (i) synthesizing a completely complementary strand of the treated target nucleic acid to provide a double-stranded nucleic acid fragment, and
      (ii) ligating an adaptor to the double-stranded nucleic acid fragment of step (i), wherein the adaptor comprises a NARS; or
   (b) if the target nucleic acid is double-stranded,
      (i) ligating an adaptor to the treated target nucleic acid, wherein the adaptor comprises a NARS.

12. The method of claim 1 wherein the NA is a restriction endonuclease (RE).

13. The method of claim 1 wherein the amplifying is performed in the presence of a strand displacement facilitator.

14. The method of claim 13 wherein the strand displacement facilitator is trehalose.

15. The method of claim 9 wherein the spectrometry is mass spectrometry.

16. The method of claim 9 wherein the chromatography is liquid chromatography.

17. The method of claim 9 wherein the characterizing is performed at least partially by liquid chromatography and mass spectrometry.

18. The method of claim 10 wherein
   (i) if the target nucleic acid is single-stranded, the first ODNP comprises a sequence completely complementary to the first nucleotide sequence of the target nucleic acid; or
   (ii) if the target nucleic acid is double-stranded, the first ODNP comprises a sequence completely complementary to the first nucleotide sequence of the first strand of the target nucleic acid.

19. The method of claim 10 wherein
   (i) if the target nucleic acid is single-stranded, the second ODNP comprises a sequence completely identical to the second nucleotide sequence of the target nucleic acid; or
   (ii) if the target nucleic acid is double-stranded, the second ODNP comprises a sequence completely complementary to the second nucleotide sequence of the second strand of the target nucleic acid.

20. The method of claim 10 wherein the first ODNP or the second ODNP is immobilized.

21. The method of claim 11 wherein the adaptor further comprises a type IIs restriction endonuclease recognition sequence (TRERS), wherein the nicking site in the template nucleic acid of a NA that recognizes the NARS is located 5' to the position corresponding to the cleavage site of a type IIs restriction endonuclease that recognizes the TRERS in the strand of the template nucleic acid that does not contain the nicking site.

22. The method of claim 21, wherein the type IIs restriction endonuclease is Bmp I.

23. The method of claim 1 wherein the single-stranded nucleic acid fragment contains no more than 17 nucleotides.

24. The method of claim 1 wherein the single-stranded nucleic acid fragment contains no more than 12 nucleotides.

25. The method of claim 11 wherein the adaptor is immobilized to a solid support.

26. The method of claim 1 wherein the providing is performed by the steps, comprising
(1) forming a mixture comprising
  (A) the treated target nucleic acid, and
  (B) an oligonucleotide primer that
    i) comprises a sequence of the sense strand of a NARS, and
    ii) is at least substantially complementary to a first portion of the treated target nucleic acid or to a first portion of one strand of the target nucleic acid; and
(2) extending the oligonucleotide primer using
  (A) a second portion of the treated single-stranded target nucleic acid located 5' to the first portion of the single-stranded target nucleic acid, or
  (B) a second portion of the one strand of the treated double-stranded nucleic acid located 5' to the first portion of the one strand of the treated double-stranded nucleic acid
as a template to provide the template nucleic acid.

27. The method of claim 26 wherein one or more nucleotides in the sense strand of the NARS do not form a conventional base pair with nucleotides of the treated single-stranded target nucleic acid or of the one strand of the treated double-stranded target nucleic acid.

28. The method of claim 26 wherein all the nucleotides in the sense strand of the NARS form conventional base pairs with nucleotides of the treat single-stranded target nucleic acid or of the one strand of the treated double-stranded target nucleic acid.

29. The method of claim 1 wherein the providing is performed by the steps, comprising
(1) forming a mixture comprising
  (A) the treated target nucleic acid,
  (B) an oligonucleotide primer that
    i) comprises a sequence of the sense strand of a NARS, and
    ii) is at least substantially complementary to a first portion of the treated target nucleic acid or to a first portion of one strand of the target nucleic acid; and
  (C) a partially double-stranded nucleic acid that
    i) comprises a double-stranded type IIs restriction endonuclease recognition sequence,
    ii) a 3' overhang that
      a) is at least substantially complementary to a second region of the single-stranded target nucleic acid located 5' to the first region of the single-stranded target nucleic acid, or
      b) is at least substantially complementary to a second region of the one strand of the double-stranded target nucleic acid located 5' to the second region of the one strand of the double-stranded target nucleic acid,
    under conditions that allow for hybridization between the oligonucleotide primer and the first region of the single-stranded target nucleic acid or of the one strand of the double-stranded nucleic acid and between the 3' overhang of the partially double-stranded nucleic acid and the second region of the single-stranded target nucleic acid or of the one strand of the double-stranded nucleic acid;
(2) digesting the single-stranded target nucleic acid or the one strand of the double-stranded target nucleic acid that have hybridized to the oligonucleotide primer and to the partially double-stranded nucleic acid in the second region; and
(3) extending from the 3' terminus of the oligonucleotide primer using the region between the first and second regions of the treated single-stranded target nucleic acid or between the first and second regions of the one strand of the treated double-stranded target nucleic acid as a template to provide the template nucleic acid.

30. The method of claim 29 wherein one or more nucleotides in the sense strand of the NARS do not form a conventional base pair with nucleotides of the treated single-stranded target nucleic acid or of the one strand of the treated double-stranded target nucleic acid.

31. The method of claim 29 wherein all the nucleotides in the sense strand of the NARS form conventional base pairs with nucleotides of the treated single-stranded target nucleic acid or of the one strand of the treated double-stranded target nucleic acid.

32. The method of claim 1 wherein the target nucleic acid is immobilized to a solid support.

33. A method for the multiplex characterization of methylation states of at least portions of target nucleic acids, comprising
  a. treating the target nucleic acids with a modifying agent that differentially modifies a nucleotide based on the methylation state of the nucleotide, to provide treated target nucleic acids;
  b. for each target nucleic acid, providing a template double-stranded nucleic acid that comprises a nicking agent recognition sequence (NARS) and a portion of the treated target nucleic acid or an amplification product thereof;
  c. amplifying single-stranded nucleic acid fragments in the presence of a nicking agent (NA) that recognizes the NARS, a DNA polymerase, and one or more deoxynucloside triphosphate(s), wherein the amplifying uses a portion of each template double-stranded nucleic acid as a template, wherein the single-stranded nucleic acid fragments each contains no more than 20 nucleotides; and
  d. characterizing the single-stranded nucleic acid fragments and thereby characterizing the methylation state of at least portions of the target nucleic acids.

34. The method of claim 33 wherein the modifying agent is a bisulfite salt.

35. The method of claim 34 wherein the modifying agent is sodium bisulfite.

36. The method of claim 33 wherein the NA is a nicking endonuclease (NE).

37. The method of claim 36 wherein the NE is N.BstNB I.

38. The method of claim 33 wherein the single-stranded target nucleic acid is one strand of a denatured double-stranded nucleic acid.

39. The method of claim 33 wherein the DNA polymerase is selected from the group consisting of exo⁻ Vent DNA polymerase, exo⁻ Deep Vent DNA polymerase, exo⁻ Bst DNA polymerase, 9°N$_m$™ DNA polymerase, and exo⁻ Bca DNA polymerase.

40. The method of claim 33 wherein the characterizing is performed at least partially by mass spectrometry.

41. The method of claim 33 wherein the characterizing is performed at least partially by liquid chromatography and mass spectrometry.

42. The method of claim 33 wherein the single-stranded nucleic acid fragments each contains no more than 17 nucleotides.

43. The method of claim 33 wherein the single-stranded nucleic acid fragments each contains no more than 12 nucleotides.

44. A method for characterizing the methylation state of a target nucleic acid, comprising:
   a. treating the target nucleic acid with a modifying agent that differentially modifies a nucleotide based on the methylation state of the nucleotide to provide a treated target nucleic acid;
   b. providing a first template double-stranded nucleic acid that comprises a nicking agent recognition sequence (NARS) and a portion of the treated target nucleic acid or an amplification product thereof if the target nucleic acid is single-stranded or a portion of one strand of the treated target nucleic acid if the target nucleic acid is double-stranded;
   c. providing a second template double-stranded nucleic acid that comprises the NARS and a portion of untreated target nucleic acid or an amplification product thereof if the target nucleic acid is single-stranded or a portion of one strand of the untreated target nucleic acid if the target nucleic acid is double-stranded;
   d. amplifying a first single-stranded nucleic acid fragment in the presence of a nicking agent (NA) that recognizes the NARS, a DNA polymerase, and one or more deoxynucleoside triphosphate(s), wherein the amplifying uses a portion of the first template double-stranded nucleic acid as a template, wherein the first single-stranded nucleic acid fragment contains no more than 20 nucleotides;
   e. amplifying a second single-stranded nucleic acid fragment in the presence of of the NA, the DNA polymerase and the deoxynucleoside triphosphate(s), wherein the amplifying uses a portion of the second template double-stranded nucleic acid as a template, wherein the second single-stranded nucleic acid fragment contains no more than 20 nucleotides;
   f. characterizing the first single-stranded nucleic acid fragment;
   g. characterizing the second single-stranded nucleic acid fragment; and
   h. comparing the characteristic of the first single-straned nucleic acid fragment obtained from step (f) with the characteristic of the second single-stranded nucleic acid fragment obtained from step (g), and thereby characterizing the methylation state of the target nucleic acid.

45. The method of claim 44 wherein the modifying agent is a bisulfite salt.

46. The method of claim 45 wherein the modifying agent is sodium bisulfite.

47. The method of claim 44 wherein the NA is a nicking endonuclease (NE).

48. The method of claim 47 wherein the NE is N.BstNB I.

49. The method of claim 44 wherein step (f) and step (g) are performed at least partially by the technique selected from the group consisting of spectrometry, chromatography, and electrophoresis.

* * * * *

SEQUENCE LISTING

<160> NUMBER OF SEQ ID NOS: 26

<210> SEQ ID NO 1
<211> LENGTH: 10
<212> TYPE: DNA
<213> ORGANISM: Artificial Sequence
<220> FEATURE:
<223> OTHER INFORMATION: Recognition sequence and nicking site of an
      exemplary nicking endonulcease, NBstNB I.
<220> FEATURE:
<221> NAME/KEY: misc_feature
<222> LOCATION: 6,7,8,9,10
<223> OTHER INFORMATION: n = A,T,C or G

<400> SEQUENCE: 1 gagtcnnnnn                                                          10

<210> SEQ ID NO 2
<211> LENGTH: 10
<212> TYPE: DNA
<213> ORGANISM: Artificial Sequence
<220> FEATURE:
<223> OTHER INFORMATION: Recognition sequence and nicking site of an
      exemplary nicking endonulcease, NBstNB I.
<220> FEATURE:
<221> NAME/KEY: misc_feature
<222> LOCATION: 1,2,3,4,5
<223> OTHER INFORMATION: n = A,T,C or G

```
<400> SEQUENCE: 2 nnnnngactc                                                              10

<210> SEQ ID NO 3
<211> LENGTH: 10
<212> TYPE: DNA
<213> ORGANISM: Artificial Sequence
<220> FEATURE:
<223> OTHER INFORMATION: Exemplary endonuclease nicking sequence that
      nicks outside its recognition sequence, N.Alwl.
<220> FEATURE:
<221> NAME/KEY: misc_feature
<222> LOCATION: 6,7,8,9,10
<223> OTHER INFORMATION: n = A,T,C or G

<400> SEQUENCE: 3 ggatcnnnnn                                                              10

<210> SEQ ID NO 4
<211> LENGTH: 10
<212> TYPE: DNA
<213> ORGANISM: Artificial Sequence
<220> FEATURE:
<223> OTHER INFORMATION: Exemplary endonuclease nicking sequence that
      nicks outside its recognition sequence, N.Alwl.
<220> FEATURE:
<221> NAME/KEY: misc_feature
<222> LOCATION: 1,2,3,4,5
<223> OTHER INFORMATION: n = A,T,C or G

<400> SEQUENCE: 4 nnnnngatcc                                                              10

<210> SEQ ID NO 5
<211> LENGTH: 33
<212> TYPE: DNA
<213> ORGANISM: Artificial Sequence
<220> FEATURE:
<223> OTHER INFORMATION: Template sequence

<400> SEQUENCE: 5
cctacgactg gaacagactc acctacgact gga                                    33

<210> SEQ ID NO 6
<211> LENGTH: 33
<212> TYPE: DNA
<213> ORGANISM: Artificial Sequence
<220> FEATURE:
<223> OTHER INFORMATION: Template sequence

<400> SEQUENCE: 6
cctacgactg gaacaataaa acctacgact gga                                    33

<210> SEQ ID NO 7
<211> LENGTH: 33
<212> TYPE: DNA
<213> ORGANISM: Artificial Sequence
<220> FEATURE:
<223> OTHER INFORMATION: Template sequence

<400> SEQUENCE: 7
cctacgactg gaacagattc acctacgact gga                                    33

<210> SEQ ID NO 8
<211> LENGTH: 33
<212> TYPE: DNA
<213> ORGANISM: Artificial Sequence
```

```
<220> FEATURE:
<223> OTHER INFORMATION: Template sequence

<400> SEQUENCE: 8
cctacgactg gaacagacac acctacgact gga                              33

<210> SEQ ID NO 9
<211> LENGTH: 33
<212> TYPE: DNA
<213> ORGANISM: Artificial Sequence
<220> FEATURE:
<223> OTHER INFORMATION: Template sequence

<400> SEQUENCE: 9
cctacgactg gaacagtctc acctacgact gga                              33

<210> SEQ ID NO 10
<211> LENGTH: 33
<212> TYPE: DNA
<213> ORGANISM: Artificial Sequence
<220> FEATURE:
<223> OTHER INFORMATION: Template sequence

<400> SEQUENCE: 10
cctacgactg gaacagaaac acctacgact gga                              33

<210> SEQ ID NO 11
<211> LENGTH: 33
<212> TYPE: DNA
<213> ORGANISM: Artificial Sequence
<220> FEATURE:
<223> OTHER INFORMATION: Template sequence

<400> SEQUENCE: 11
cctacgactg gaacagtaac acctacgact gga                              33

<210> SEQ ID NO 12
<211> LENGTH: 33
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 12
tccagtcgta ggtgagtctg ttccagtcgt agg                              33

<210> SEQ ID NO 13
<211> LENGTH: 32
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 13
ccagtcgtag gtgagtctgt tccagtcgta gg                               32

<210> SEQ ID NO 14
<211> LENGTH: 31
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 14
```
cagtcgtagg tgagtctgtt ccagtcgtag g                                      31

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 15
agtcgtaggt gagtctgttc cagtcgtagg                                        30

<210> SEQ ID NO 16
<211> LENGTH: 29
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 16
gtcgtaggtg agtctgttcc agtcgtagg                                         29

<210> SEQ ID NO 17
<211> LENGTH: 28
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 17
tcgtaggtga gtctgttcca gtcgtagg                                          28

<210> SEQ ID NO 18
<211> LENGTH: 27
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 18
cgtaggtgag tctgttccag tcgtagg                                           27

<210> SEQ ID NO 19
<211> LENGTH: 26
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 19
gtaggtgagt ctgttccagt cgtagg                                            26

<210> SEQ ID NO 20
<211> LENGTH: 25
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 20

```
taggtgagtc tgttccagtc gtagg                                           25
```

<210> SEQ ID NO 21
<211> LENGTH: 24
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 21

```
aggtgagtct gttccagtcg tagg                                            24
```

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 22

```
ggtgagtctg ttccagtcgt agg                                             23
```

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 23

```
gtgagtctgt tccagtcgta gg                                              22
```

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 24

```
tgagtctgtt ccagtcgtag g                                               21
```

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide sequence complimentary to
      template used for amplification

<400> SEQUENCE: 25

```
gagtctgttc cagtcgtagg                                                 20
```

<210> SEQ ID NO 26
<211> LENGTH: 11
<212> TYPE: DNA
<213> ORGANISM: Artificial Sequence
<220> FEATURE:
<223> OTHER INFORMATION: Amplification product

<400> SEQUENCE: 26

```
ccagtcgtag g                                                          11
```